US011471442B2

(12) United States Patent
Borin et al.

(10) Patent No.: US 11,471,442 B2
(45) Date of Patent: Oct. 18, 2022

(54) ADMINISTRATION OF GUT-SELECTIVE JAK3 INHIBITOR

(71) Applicant: THERAVANCE BIOPHARMA R&D IP, LLC, South San Francisco, CA (US)

(72) Inventors: Marie T. Borin, South San Francisco, CA (US); David L. Bourdet, South San Francisco, CA (US); Ai Ling Ching, South San Francisco, CA (US); Arthur Lo, South San Francisco, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 3 days.

(21) Appl. No.: 17/315,898

(22) Filed: May 10, 2021

(65) Prior Publication Data
US 2021/0353597 A1    Nov. 18, 2021

Related U.S. Application Data

(60) Provisional application No. 63/024,769, filed on May 14, 2020, provisional application No. 63/048,229, filed on Jul. 6, 2020, provisional application No. 63/086,854, filed on Oct. 2, 2020.

(51) Int. Cl.
| A61K 31/397 | (2006.01) |
| A61K 31/416 | (2006.01) |
| A61P 1/00 | (2006.01) |
| C07D 403/12 | (2006.01) |

(52) U.S. Cl.
CPC .................. *A61K 31/416* (2013.01)

(58) Field of Classification Search
CPC ....... A61K 31/397; A61K 31/416; A61P 1/00; C07D 403/12
See application file for complete search history.

(56) References Cited

U.S. PATENT DOCUMENTS

| 10,392,368 B2 | 8/2019 | Fenster |
| 10,538,513 B2 | 1/2020 | McKinnell |
| 10,968,205 B2 | 4/2021 | McKinnell |
| 2019/0315724 A1 | 10/2019 | McKinnell |
| 2019/0389895 A1 | 12/2019 | Hudson |

FOREIGN PATENT DOCUMENTS

WO    2013017480    2/2013

OTHER PUBLICATIONS

Goedken, et al., "Tricyclic Covalent Inhibitors Selectively Target Jak3 trhough an Active Site Thiol*," The Journal of Biological Chemistry, vol. 290, No. 8, pp. 4573-4589, Feb. 20, 2015.
Borin et al., "Safety and Pharmacokinetics of the Gut-selective Janus Kinase 3 Covalent Inhibitor TD-5202 in Healthy Subjects", Theravance Biopharma, ueg week, virtual 2020, 1 page.
Coghill et al., "Effector CD4+ T cells, the cytokines they generate, and GVHD: something old and something new", Blood, Mar. 24, 2011, vol. 117, No. 12, 10 pages.
De Nitto et al., "Involvement of interleukin-15 and interleukin-21, two y-chain-related cytokines, in celiac disease", World J Gastroenterol, Oct. 7, 2009, 15(37), 4609-4614, 6 pages.
Kumawat et al., "Microscopic colitis patients demonstrate a mixed Th17/Tc17 and Th1/Tc1 mucosal cytokine profile", Molecular Immunology, 55 (2013) 355-364, 10 pages.
Reimund et al., "Mucosal Inflammatory Cytokine Production by Intestinal Biopsies in Patients with Ulcerative Colitis and Crohn's Disease", Journal of Clinical Immunology, vol. 16, No. 3, 1996, 7 pages.
Single and Multiple Ascending Dose, First-in-Human Study in Healthy Subjects, ClinicalTrials.gov Identifier: NCT04044339, https://clinicaltrials.gov/ct2/show/record/NCT04044339?term=TD-5202&draw=2&rank=1, 8 pages, 2019.
Stallmach et al., "Cytokine/chemokine transcript profiles reflect mucosal inflammation in Crohn's disease", Int J Colorectal Dis (2004) 19:308-315 DOI 10.1007/S00384-003-0554-4, 8 pages.
Strober et al., "Pro-Inflammatory Cytokines in the Pathogenesis of IBD", Gastroenterology. May 2011 ; 140(6): 1756-1767. doi:10.1053/j.gastro.2011.02.016, 20 pages.
United European Gastroenterology Journal, "An international forum for clinical practice and research in gastroenterology, Abstract issue", Oct. 2020, vol. 8, Issue 8, journals.sagepub.com/home/ueg, 28th United European Gastroenterology Week Virtual 2020, 4 pages.
Weinbrand-Goichberg et al., "Eosinophilic esophagitis: an immune-mediated esophageal disease", Immunol Res (2013) 56:249-260 DOI: 10.1007/s12026-013-8394-y, 12 pages.
Woywodt et al., "Mucosal cytokine expression, cellular markers and adhesion molecules in inflammatory bowel disease", European Journal of Gastroenterology & Hepatology 1999,11:267-276, 10 pages.
Yamamoto et al., "Mucosal inflammation in the terminal ileum of ulcerative colitis patients: Endoscopic findings and cytokine profiles", Digestive and Liver Disease 40 (2008) 253-259, www.sciencedirect.com, 7 pages.
Yano et al., "Ipilimumab augments antitumor activity of bispecific antibody-armed T cells", Journal of Translational Medicine 2014, 12:191 http://www.translational-medicine.com/content/12/1/191, 11 pages.
Zhou et al., "Cytokines and Behcet's Disease", Autoimmunity Reviews 11 (2012) 699-704, 6 pages.
Danese et al., "Ulcerative Colitis", N Engl J Med 2011;365:1713-25, 13 pages.
Silvio Danese, "New therapies for inflammatory bowel disease: from the bench to the bedside", Gut 2012;61:918e932. doi:10.1136/gutjnl-2011-300904, 16 pages.

(Continued)

*Primary Examiner* — Brenda L Coleman
(74) *Attorney, Agent, or Firm* — Ice Miller LLP

(57) ABSTRACT

Methods of safely administrating a gut-selective JAK3 inhibitor by oral administration are described. Also described are methods for providing clinically proven safe treatment of gastrointestinal inflammatory diseases, such as celiac disease, by oral administration of a gut-selective JAK3 inhibitor.

20 Claims, 7 Drawing Sheets

(56) References Cited

OTHER PUBLICATIONS

Lam et al., "Vedolizumab for ulcerative colitis and Crohn's disease: results and implications of Gemini studies", Immunotherapy (2014) 6(9), 963-971, 9 pages.

Mozaffari et al., "New biologic therapeutics for ulcerative colitis and Crohn's disease", Expert Opin. Biol. Ther. (2014) 14(5):583-600, 18 pages.

Theravance Biopharma, Inc. Reports Fourth Quarter and Full-Year 2019 Financial Results and Provides Business Update, Feb. 24, 2020, 5 pages.

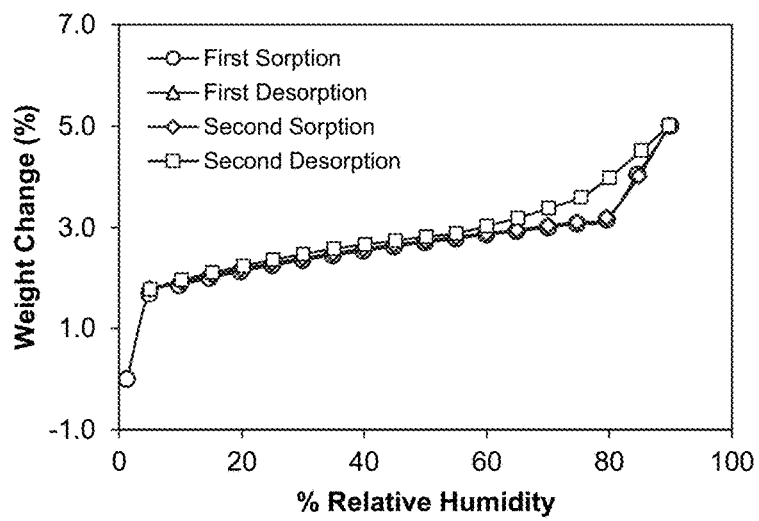
FIG. 9
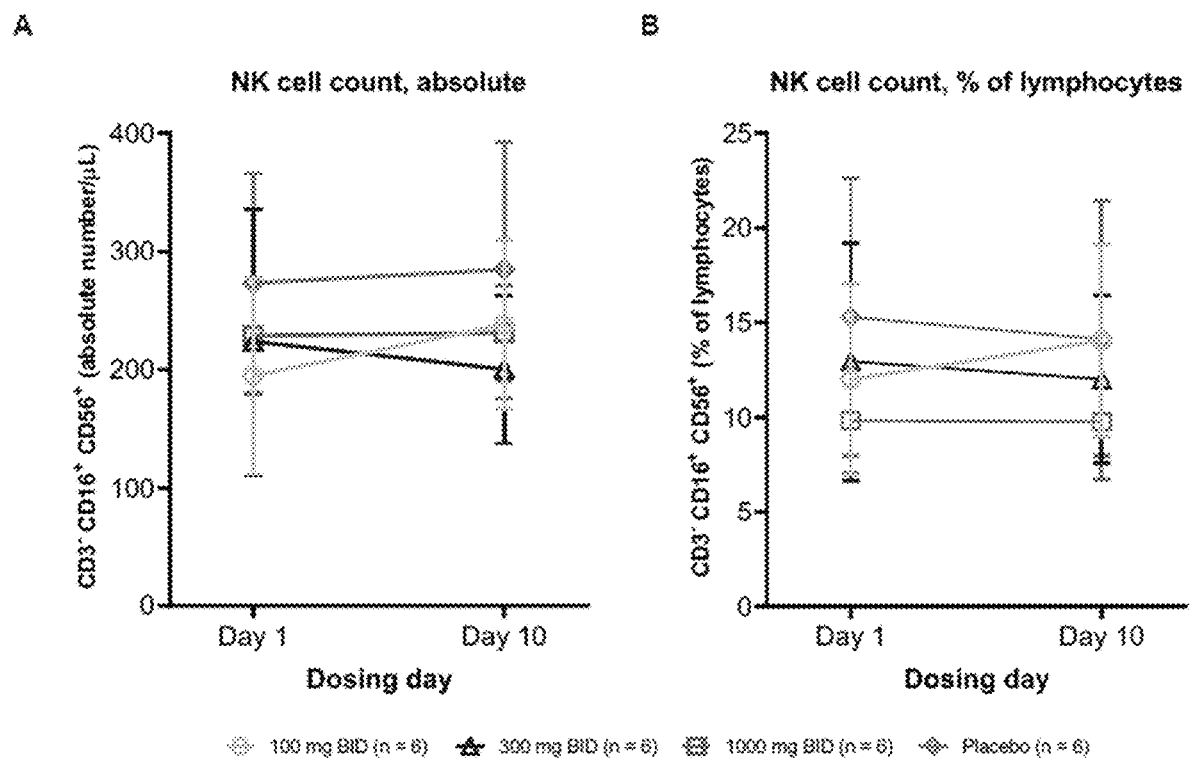
FIGs.10A-B

ADMINISTRATION OF GUT-SELECTIVE JAK3 INHIBITOR

CROSS REFERENCE TO RELATED APPLICATIONS

This application claims priority to U.S. Provisional Patent Application No. 63/024,769, filed on May 14, 2020, U.S. Provisional Patent Application No. 63/048,229, filed Jul. 6, 2020, and U.S. Provisional Patent Application No. 63/086,854, filed Oct. 2, 2020, the disclosures of which are incorporated herein by reference.

FIELD

The application relates to methods of safely administrating a gut-selective JAK3 inhibitor and methods of providing clinically proven safe treatment of gastrointestinal inflammatory diseases by oral administration of a gut-selective JAK3 inhibitor.

BACKGROUND

Ulcerative colitis is a chronic inflammatory disease of the colon. The disease is characterized by inflammation and ulceration of the mucosal layer of the rectum and the large intestine. Common symptoms include diarrhea, bloody stools, and abdominal pain. The clinical course is intermittent, marked by alternating periods of exacerbation and remission. Incidence seems to be greater in developed than in developing countries. An estimated 1.2 million people in major industrialized countries suffer from ulcerative colitis and the numbers are expected to increase along with population growth. Patients with ulcerative colitis are at an increased risk of developing colorectal cancer (e.g. Danese et al. *N Engl J Med,* 2011, 365, 1713-1725). Although there exists a variety of therapeutic options to promote and maintain remission of ulcerative colitis (UC) in patients, none is ideal. There remains an unmet medical need for an effective therapy to promote and maintain remission of moderate to severe UC without the safety concerns resulting from chronic, systemic immunosuppression.

Although the precise pathogenesis of UC is unclear, it is apparent that proinflammatory cytokines play a pivotal role in the immunological response (Strober et al., *Gastroenterol,* 2011, 140, 1756-1767). Many of the proinflammatory cytokines most commonly elevated in UC (e.g., IL-4, IL-6, IL-13, IL-15, IL-23, IL-24, IFNγ and leptin), rely on the JAK family of tyrosine kinases (i.e., JAK1, JAK2, JAK3 and Tyk2) for signal transduction.

Inhibition of the JAK3 enzyme blocks the signaling of many key pro-inflammatory cytokines. Thus, JAK3 inhibitors are likely to be useful in the treatment of ulcerative colitis and other gastrointestinal inflammatory diseases such as celiac disease and immune checkpoint inhibitor induced colitis. JAK3 inhibitors are also likely to be useful for the treatment of inflammatory skin diseases such as atopic dermatitis and inflammatory respiratory disorders such as allergic rhinitis, asthma, and chronic obstructive pulmonary disease (COPD). In addition, JAK3 inhibitors may also be useful in the treatment of many ocular diseases for which inflammation plays a prominent role such as uveitis, diabetic retinopathy, diabetic macular edema, dry eye disease, age-related macular degeneration, retinal vein occlusion (RVO) and atopic keratoconjunctivitis.

For some conditions, selectivity for JAK3 over JAK1 is anticipated to be beneficial as there is evidence that JAK3 selectivity allows sparing of potentially beneficial cytokines, such as IL-10 which has been involved in mucosal healing, IL-22 which is involved in mucus barrier protection and epithelial regeneration, and IL-6 which is involved in the proliferation of intestinal epithelial cells. Selectivity for JAK3 over JAK2 also allows sparing of erythropoietin (EPO) and thrombopoietin (TPO) signaling. Therefore, it would be desirable to provide new treatments with compounds that are selective JAK3 inhibitors over other members of the JAK kinase family such as JAK1, JAK2 and TYK2.

Finally, due to the modulating effect of the JAK/STAT pathway on the immune system, systemic exposure to JAK inhibitors may have an adverse systemic immunosuppressive effect. For example, consider Tofacitinib (Xeljanz®), which is an oral, systemically available pan-JAK inhibitor approved in the US for patients with moderate to severe ulcerative colitis, psoriatic arthritis, and rheumatoid arthritis. While this treatment demonstrated efficacy in Phase 2 and Phase 3 clinical trials, clinical data in rheumatoid arthritis patients has raised concern that dose-limiting, systemically-mediated, adverse events may prove to be an issue, either acutely or chronically (e.g., increased cholesterol levels, increased rate of opportunistic infections, neutropenia, lymphocytopenia, lymphoma and solid tumors). To this end, rheumatoid arthritis and ulcerative colitis patients receiving tofacitinib (Xeljanz®) have experienced thromboembolic events including venous thrombosis (including but not limited to deep vein thrombosis), pulmonary embolism, cerebrovascular events and arterial thrombosis; malignancy; lymphopenia; neutropenia; liver enzyme elevations; lipid elevations; serum creatinine elevations; and serious infections. Accordingly, it remains to be determined whether any of the putative JAK subtype-selective inhibitors in development (e.g., filgotinib and upadacitinib) will have a more favorable safety profile than that of tofacitinib.

It would be desirable, therefore, to provide new treatments with JAK3 inhibitors which have their effect at the site of action without significant systemic effects. In particular, for the treatment of gastrointestinal inflammatory diseases, it would be desirable to use JAK3 inhibitors which can be administered orally and achieve therapeutically relevant exposure in the gastrointestinal tract with minimal systemic exposure.

Therefore, it would be desirable to provide new treatments involving selective JAK3 inhibitors over other members of the JAK kinase family such as JAK1, JAK2 and TYK2, which have minimal systemic exposure.

BRIEF SUMMARY

Disclosed herein are methods of safely administrating a gut-selective JAK3 inhibitor to subjects, including clinically proven safe treatment of a gastrointestinal inflammatory disease, such as celiac disease.

In one general aspect, the described herein is a method of safely administrating a compound of formula (I):

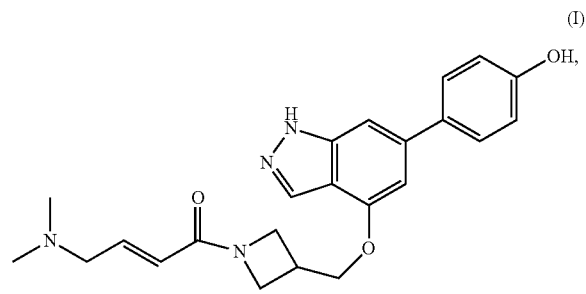 [SMILES: CN(C)C/C=C/C(=O)N1CC(COc2cc(-c3ccc(O)cc3)cc3[nH]ncc23)C1]

or a pharmaceutically acceptable salt thereof, to a human subject in need thereof, comprising orally administering to the subject a pharmaceutical composition comprising the compound of formula (I) or the pharmaceutically acceptable salt thereof and a pharmaceutically acceptable carrier.

In some embodiments, a total dosage of the compound of formula (I) or the pharmaceutically acceptable salt thereof administered is about 100 mg to about 2000 mg per administration.

In some embodiments, a total dosage of the compound of formula (I) or the pharmaceutically acceptable salt thereof administered per administration is about 100 mg, 150 mg, 200 mg, 300 mg, 400 mg, 500 mg, 600 mg, 700 mg, 800 mg, 900 mg, 1000 mg, 1250 mg, 1500 mg, 1750 mg, or 2000 mg, or any dosage in between.

In some embodiments, the pharmaceutical composition is administered once per day. In such embodiments, the total dosage of the compound of formula (I) or the pharmaceutically acceptable salt thereof administered per day is about 100 mg, 150 mg, 200 mg, 300 mg, 400 mg, 500 mg, 600 mg, 700 mg, 800 mg, 900 mg, 1000 mg, 1250 mg, 1500 mg, 1750 mg, or 2000 mg, or any dosage in between.

In some embodiments, the pharmaceutical composition is administered once per day. In such embodiments, the total dosage of the compound of formula (I) or the pharmaceutically acceptable salt thereof administered per day is about 500 mg to about 700 mg, or any dosage in between.

In some embodiments, the pharmaceutical composition is administered once per day. In such embodiments, the total dosage of the compound of formula (I) or the pharmaceutically acceptable salt thereof administered per day is about 550 mg to about 650 mg, or any dosage in between.

In some embodiments, the pharmaceutical composition is administered once per day. In such embodiments, the total dosage of the compound of formula (I) or the pharmaceutically acceptable salt thereof administered per day is about 500 mg to about 600 mg, or any dosage in between.

In some embodiments, the pharmaceutical composition is administered once per day. In such embodiments, the total dosage of the compound of formula (I) or the pharmaceutically acceptable salt thereof administered per day is about 500 mg.

In some embodiments, the pharmaceutical composition is administered once per day. In such embodiments, the total dosage of the compound of formula (I) or the pharmaceutically acceptable salt thereof administered per day is about 550 mg.

In certain embodiments, when the pharmaceutical composition is orally administered once per day, the total dosage of the compound of formula (I) or the pharmaceutically acceptable salt thereof administered per administration is about 600 mg.

In some embodiments, the pharmaceutical composition is administered twice per day. In such embodiments, the total dosage of the compound of formula (I) or the pharmaceutically acceptable salt thereof administered per administration is about 100 mg, 150 mg, 200 mg, 300 mg, 400 mg, 500 mg, 600 mg, 700 mg, 800 mg, 900 mg, or 1000 mg, or any dosage in between.

In some embodiments, when the pharmaceutical composition is orally administered twice per day, the total dosage of the compound of formula (I) or the pharmaceutically acceptable salt thereof administered per day is about 200 mg, 300 mg, 400 mg, 500 mg, 600 mg, 700 mg, 800 mg, 900 mg, 1000 mg, 1250 mg, 1500 mg, 1750 mg, or 2000 mg, or any dosage in between.

In certain embodiments, when the pharmaceutical composition is orally administered twice per day, the total dosage of the compound of formula (I) or the pharmaceutically acceptable salt thereof administered per administration is about 250 mg.

In certain embodiments, when the pharmaceutical composition is orally administered twice per day, the total dosage of the compound of formula (I) or the pharmaceutically acceptable salt thereof administered per administration is about 275 mg.

In certain embodiments, when the pharmaceutical composition is orally administered twice per day, the total dosage of the compound of formula (I) or the pharmaceutically acceptable salt thereof administered per administration is about 300 mg.

In some embodiments, the administration of the pharmaceutical composition does not result in a serious adverse effect. In certain embodiments, the serious adverse effect comprises a thromboembolic event, a malignancy, lymphopenia, neutropenia, liver enzyme elevation, lipid elevation, serum creatinine elevation, or a serious infection.

In some embodiments, the administration of the pharmaceutical composition does not result in clinically significant changes from the predose baseline in a laboratory assessment, a vital sign or an electrocardiogram (ECG).

In some embodiments, the human subject is in need of a treatment of a gastrointestinal inflammatory disease. In certain embodiments, the gastrointestinal inflammatory disease is immune checkpoint inhibitor induced colitis, CTLA-4 inhibitor-induced colitis, graft versus host disease-related colitis, celiac disease, collagenous colitis, lymphocytic colitis, Behcet's disease, ileitis, eosinophilic esophagitis, or infectious colitis.

In another general aspect, the invention relates to a method of treating a gastrointestinal inflammatory disease in a human subject in need thereof, the method comprising orally administering to the subject a compound of formula (I):

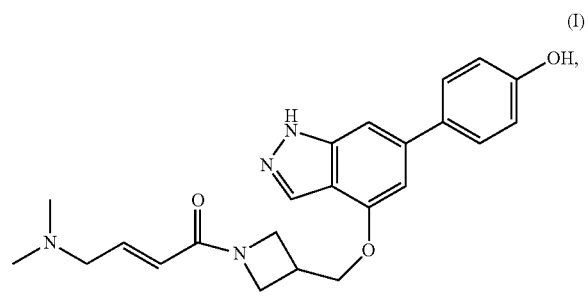 [SMILES: CN(C)C/C=C/C(=O)N1CC(COc2cc(-c3ccc(O)cc3)cc3[nH]ncc23)C1]

or a pharmaceutically acceptable salt thereof, wherein the compound of formula (I), or the pharmaceutically acceptable salt thereof, is administered to the subject in an amount sufficient to provide from about 500 mg per day to about 2000 mg per day of the compound of formula (I) or a pharmaceutically acceptable salt thereof.

In another general aspect, the invention relates to a method of treating a gastrointestinal inflammatory disease in a human subject in need thereof, the method comprising orally administering to the subject a pharmaceutical composition comprising a pharmaceutically acceptable carrier and a compound of formula (I):

(I)

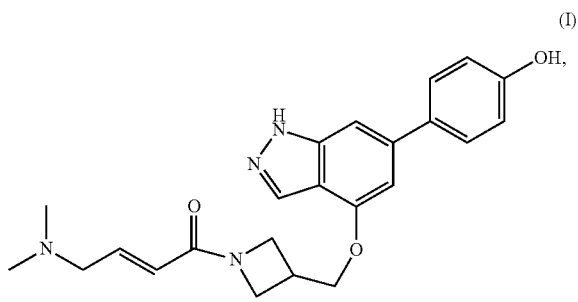 [SMILES: CN(C)C/C=C/C(=O)N1CC(COc2cc(-c3ccc(O)cc3)cc3[nH]ncc23)C1]

or a pharmaceutically acceptable salt thereof, wherein the pharmaceutical composition is administered to the subject in an amount sufficient to provide from about 500 mg per day to about 2000 mg per day of the compound of formula (I) or a pharmaceutically acceptable salt thereof.

In another general aspect, the invention relates to a compound of formula (I):

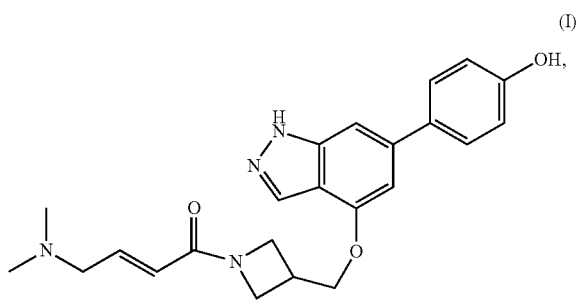 [SMILES: CN(C)C/C=C/C(=O)N1CC(COc2cc(-c3ccc(O)cc3)cc3[nH]ncc23)C1]

or a pharmaceutically acceptable salt thereof, for use in the treatment of a gastrointestinal inflammatory disease in a human subject, wherein the compound of formula (I), or the pharmaceutically acceptable salt thereof, is orally administered to the subject in an amount sufficient to provide from about 500 mg per day to about 2000 mg per day of the compound of formula (I) or a pharmaceutically acceptable salt thereof.

In another general aspect, the invention relates to a pharmaceutical composition comprising a pharmaceutically acceptable carrier and a compound of formula (I):

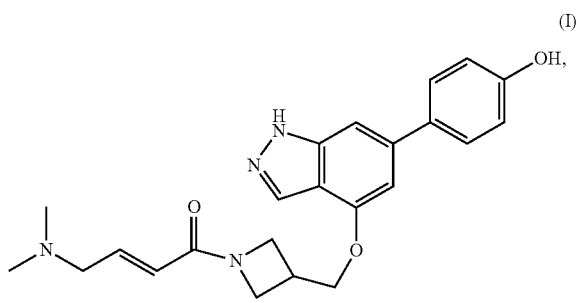 [SMILES: CN(C)C/C=C/C(=O)N1CC(COc2cc(-c3ccc(O)cc3)cc3[nH]ncc23)C1]

or a pharmaceutically acceptable salt thereof, for use in the treatment of a gastrointestinal inflammatory disease in a human subject, wherein the composition is orally administered to the subject in an amount sufficient to provide from about 500 mg per day to about 2000 mg per day of the compound of formula (I) or a pharmaceutically acceptable salt thereof.

In another general aspect, the invention relates to use of a compound of formula (I):

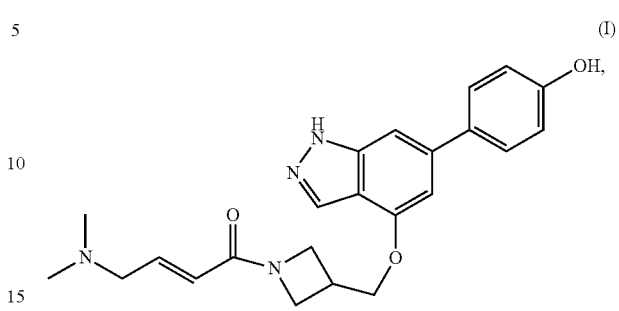

or a pharmaceutically acceptable salt thereof, in the manufacture of a medicament for the treatment of a gastrointestinal inflammatory disease in a human subject, wherein the compound of formula (I), or the pharmaceutically acceptable salt thereof, is orally administered to the subject in an amount sufficient to provide from about 500 mg per day to about 2000 mg per day of the compound of formula (I) or a pharmaceutically acceptable salt thereof.

In another general aspect, the invention relates to use of a pharmaceutical composition comprising a pharmaceutically acceptable carrier and a compound of formula (I):

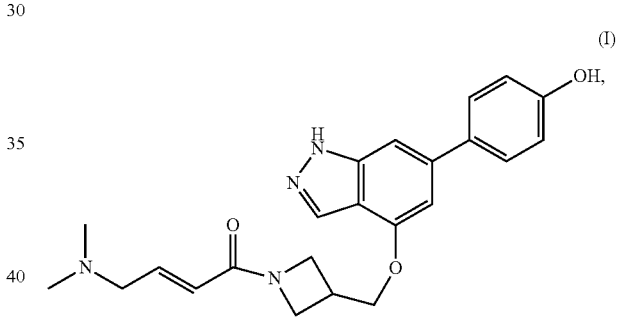

or a pharmaceutically acceptable salt thereof, in the manufacture of a medicament for the treatment of a gastrointestinal inflammatory disease in a human subject, wherein the pharmaceutical composition is orally administered to the subject in an amount sufficient to provide from about 500 mg per day to about 2000 mg per day of the compound of formula (I) or a pharmaceutically acceptable salt thereof.

The following embodiments apply to each of the general aspects disclosed herein, including the above-described general aspects.

In some embodiments, the gastrointestinal inflammatory disease is immune checkpoint inhibitor induced colitis, CTLA-4 inhibitor-induced colitis, graft versus host disease-related colitis, celiac disease, collagenous colitis, lymphocytic colitis, Behcet's disease, ileitis, eosinophilic esophagitis, or infectious colitis. In a particular embodiment, the gastrointestinal inflammatory disease is celiac disease.

In one embodiment, the treatment is a clinically proven safe treatment.

In some embodiments, the compound of formula (I), or a pharmaceutically acceptable salt thereof, is administered once per day. In such embodiments, the compound or the salt thereof is administered to the subject in an amount sufficient to provide about 500 mg per day, 600 mg per day, 700 mg per day, 800 mg per day, 900 mg per day, or 1000 mg per day of the compound of formula (I) or a pharmaceutically acceptable salt.

In some embodiments, the pharmaceutical composition is administered once per day. In such embodiments, the pharmaceutical composition is administered to the subject in an amount sufficient to provide about 500 mg per day, 600 mg per day, 700 mg per day, 800 mg per day, 900 mg per day, or 1000 mg per day of the compound of formula (I) or a pharmaceutically acceptable salt.

In some embodiments, the compound of formula (I), or a pharmaceutically acceptable salt thereof, is administered twice per day. In such embodiments, the compound or the salt thereof is administered to the subject twice per day in an amount sufficient to provide about 500 mg per day, 600 mg per day, 700 mg per day, 800 mg per day, 900 mg per day, or 1000 mg per day of the compound of formula (I) or a pharmaceutically acceptable salt.

In some embodiments, the pharmaceutical composition is administered twice per day. In such embodiments, the pharmaceutical composition is administered to the subject twice per day in an amount sufficient to provide about 500 mg per day, 600 mg per day, 700 mg per day, 800 mg per day, 900 mg per day, or 1000 mg per day of the compound of formula (I) or a pharmaceutically acceptable salt.

The details of one or more embodiments of the invention are set forth in the description below. Other features and advantages will be apparent from the following detailed description, and the appended claims.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

FIG. 9 shows a dynamic moisture sorption (DMS) isotherm of crystalline Form 4 observed at a temperature of about 25° C.

FIGS. 10A-B demonstrate the NK cell counts from day 1 to day 10 in the multiple ascending doses (MAD) cohorts—FIG. 10A: absolute NK cell counts, FIG. 10B: relative NK cell counts.

In FIG. 11A, inset shows expansion of the first 12 hours postdose on day 1, and in the 100 mg cohort, n is 4 at 72 hours because the concentration was below the limit of quantification in 2 subjects. In FIG. 11B, gray box indicates day 1 of MAD portion. Symbols and error bars represent the arithmetic mean plus SD, and reference $IC_{50}$ values shown are from data on file. BID, twice daily; HuPBMC, human peripheral blood mononuclear cell; $IC_{50}$, concentration producing 50% of maximal inhibition.

DETAILED DESCRIPTION

Figure 1:
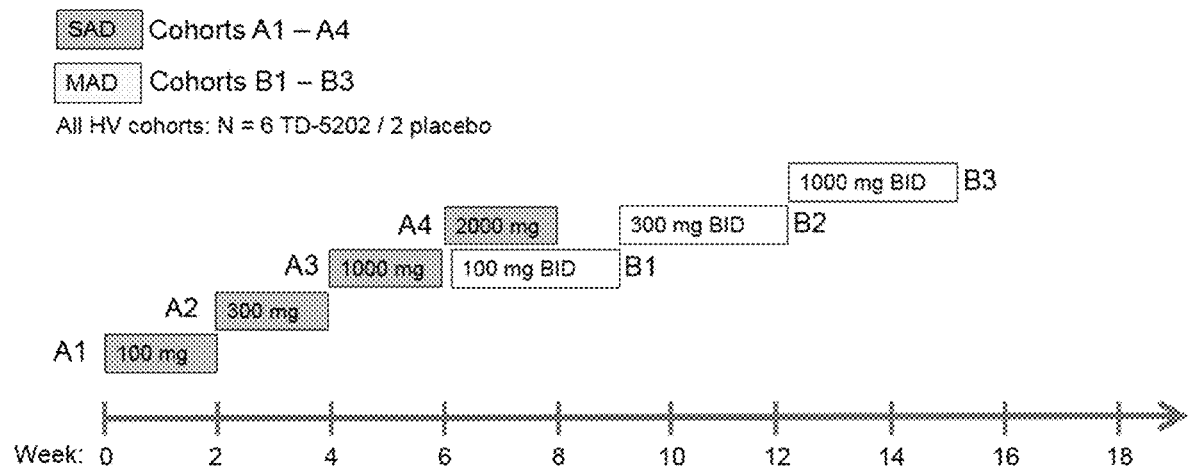
FIG. 1 shows a diagrammatic representation of the study design of a clinical study using the compound of formula (I).

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

Definitions

It must be noted that as used herein and in the appended claims, the singular forms "a," "an," and "the" include plural reference unless the context clearly dictates otherwise.

As used herein, the term "about" preceding a numerical value or a series of numerical values means ±10% of the numerical value unless otherwise indicated. For example, "about 100 mg" means 90 to 110 mg.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or." As used herein, unless otherwise noted, the term "clinically proven" (used independently or to modify the term "safe") shall mean that it has been proven by a clinical study in human subjects wherein the clinical study has met the approval standards of U.S. Food and Drug Administration, European Medicines Evaluation Agency (EMEA), or a corresponding national regulatory agency. In one embodiment of the application, the clinical study is a first-in-human, randomized, double-blind, placebo-controlled, single and multiple ascending dose study of the compound of formula (I), which is a JAK3 inhibitor, in healthy human subjects.

As used herein, the phrases "adverse event (AE)," "treatment-emergent adverse event," "adverse reaction," and "adverse effect" mean any harm, unfavorable, unintended or undesired sign or outcome associated with or caused by administration of a pharmaceutical composition or therapeutic. However, abnormal values or observations are not reported as adverse events unless considered clinically significant by an investigator or a medical doctor. Examples of adverse events or reactions when used in the context of oral administration of a JAK3 inhibitor include, but are not limited to, bladder pain, bloody or cloudy urine, blurred vision, body aches or pain, chills cough, difficult or burning or painful urination, diarrhea, difficulty breathing, dizziness, ear congestion, fever, frequent urge to urinate, headache, loss of voice, lower back or side pain, muscle aches, nervousness, pounding in the ears, slow or fast heartbeat, sneezing, sore throat, stomach discomfort or upset or pain, stuffy or runny nose, tenderness in the stomach area, and unusual tiredness or weakness.

As used herein, the phrases "serious adverse event (SAE)" and "serious adverse effect" mean any adverse event that is serious, as defined by the Food and Drug Administration (FDA) Code of Federal Regulations (CFR), Chapter 21. A SAE can be any AE or suspected adverse reaction that in the view of an investigator or a medical doctor, results in any of the following outcomes: death, a life threatening adverse event, inpatient hospitalization or prolongation of existing hospitalization, a persistent or significant incapacity or substantial disruption of the ability to conduct normal life functions, or a congenital anomaly/birth defect. Important medical events that may not result in death, be life threatening, or require hospitalization may be considered serious when, based upon appropriate medical judgment, they may jeopardize the patient or subject and may require medical or surgical intervention to prevent one of the outcomes listed in the above definition. Examples of such medical events include allergic bronchospasm requiring intensive treatment in an emergency room or at home, blood dyscrasias or convulsions that do not result in inpatient hospitalization, or the development of drug dependency or drug abuse.

Serious adverse event can be, but not limited to, a thromboembolic event, pulmonary embolism, cerebrovascular events and arterial thrombosis, a malignancy, lymphopenia, neutropenia, liver enzyme elevation, lipid elevation, serum creatinine elevation, or a serious infection, which had reported for a compound (tofacitinib) in this same drug class (Xeljanz® (tofacitinib) Prescribing Information. N.Y.: Pfizer Labs; 2019).

As used herein, when referring to safety assessment of the administration of the JAK3 inhibitor, "clinically significant changes" means clinically apparent changes as determined by a medical doctor or an investigator using standard acceptable to those of ordinary skill in the art. When the harm or undesired outcome of adverse events reaches such a level of severity, a regulatory agency can deem the pharmaceutical composition or therapeutic unacceptable for the proposed use. Such changes can be measured by physical examination, such as examination of respiratory, cardiovascular, and gastrointestinal systems; laboratory assessments, such as particular lipid, coagulation, hematology, and natural killer (NK) cell counts; vital signs, such as body temperature, respiratory rate, blood pressure and heart rate; and electrocardiogram (ECG) monitoring, including 12 lead safety ECGs and Holter monitoring for cardiodynamic assessment.

As used herein, "treatment" or "treat" refers to the treatment of a disease, disorder, or medical condition (such as a gastrointestinal inflammatory disease), in a patient, such as a mammal (particularly a human) which includes one or more of the following:
 (a) preventing the disease, disorder, or medical condition from occurring, i.e., preventing the reoccurrence of the disease or medical condition or prophylactic treatment of a patient that is pre-disposed to the disease or medical condition;
 (b) ameliorating the disease, disorder, or medical condition, i.e., eliminating or causing regression of the disease, disorder, or medical condition in a patient, including counteracting the effects of other therapeutic agents;
 (c) suppressing the disease, disorder, or medical condition, i.e., slowing or arresting the development of the disease, disorder, or medical condition in a patient; or
 (d) alleviating the symptoms of the disease, disorder, or medical condition in a patient.

The terms "efficacy" and "effective" as used herein in the context of a dose, dosage regimen, treatment or method refer to the effectiveness of a particular dose, dosage or treatment regimen. Efficacy can be measured based on change in the course of the disease in response to an agent of the present invention. For example, the compound of formula (I) can be administered to a subject in an amount and for a time sufficient to induce an improvement, preferably a sustained improvement, in at least one indicator that reflects the severity of the disorder that is being treated. Various indicators that reflect the extent of the subject's illness, disease or condition can be assessed for determining whether the amount and time of the treatment is sufficient. Such indicators include, for example, clinically recognized indicators of disease severity, symptoms, or manifestations of the disorder in question. The degree of improvement generally is determined by a physician, who can make this determination based on signs, symptoms, biopsies, or other test results, and who can also employ questionnaires that are administered to the subject, such as quality-of-life questionnaires developed for a given disease. For example, the compound of formula (I) can be administered to achieve an improvement in a subject's condition related to gastrointestinal inflammatory disease.

The term "therapeutically effective amount" means an amount sufficient to effect treatment when administered to a patient in need of treatment.

Methods of Safe Administration

In one general aspect, the invention relates to a method of safely administrating a compound of formula (I):

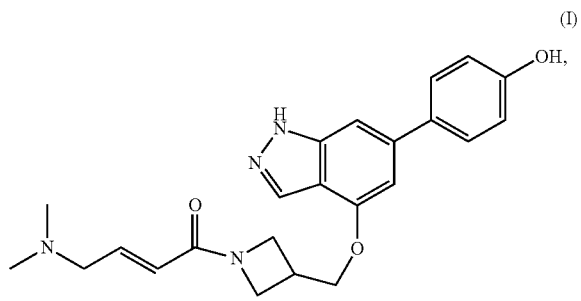 [SMILES: CN(C)C/C=C/C(=O)N1CC(COc2cc(-c3ccc(O)cc3)cc3[nH]ncc23)C1]

or a pharmaceutically acceptable salt thereof, to a human subject in need thereof, comprising orally administering to the subject a pharmaceutical composition comprising the compound of formula (I) or the pharmaceutically acceptable salt thereof and a pharmaceutically acceptable carrier.

According to the embodiments of the invention, the compound of formula (I) has activity as a JAK kinase inhibitor and more particularly as a gut-selective JAK3 inhibitor. The compound of formula (I), its synthesis, crystalline forms, biologic activities, uses or other related information thereof are described, for example, in International Patent Application Publication No. WO 2019/027960, published on Feb. 7, 2019, the content of which is hereby incorporated by reference in its entireties.

In one embodiment, the pharmaceutical composition is administered to the subject in an amount sufficient to provide from about 100 mg per day to about 2000 mg per day of the compound of formula (I) or a pharmaceutically acceptable salt thereof. In another embodiment, the pharmaceutical composition is administered to the subject in an amount sufficient to provide from about 500 mg per day to about 1000 mg per day, for example, 500 mg per day, 600 mg per day, 700 mg per day, 800 mg per day, 900 mg per day, 1000 mg per day, of the compound of formula (I) or a pharmaceutically acceptable salt thereof.

According to the embodiments of the invention, the pharmaceutical composition can be administered once per day, twice per day, three times per day, once per week, twice per week, etc.

The total dosage of the compound of formula (I) or the pharmaceutically acceptable salt thereof per administration is selected so as to provide safe administration and/or safe treatment by oral administration as determined in clinical trials. According to embodiments of the invention, a total dosage of the compound of formula (I) or the pharmaceutically acceptable salt thereof administered orally is from about 100 mg to about 2000 mg per administration, for example, 100 mg, 150 mg, 200 mg, 300 mg, 400 mg, 500 mg, 600 mg, 700 mg, 800 mg, 900 mg, 1000 mg, 1250 mg, 1500 mg, 1750 mg, or 2000 mg, or any dosage in between.

In some embodiments, the pharmaceutical composition is orally administered once per day.

In such embodiments, the total dosage of the compound of formula (I) or the pharmaceutically acceptable salt thereof administered per day is about 100 mg, 150 mg, 200 mg, 300 mg, 400 mg, 500 mg, 600 mg, 700 mg, 800 mg, 900 mg, 1000 mg, 1250 mg, 1500 mg, 1750 mg, or 2000 mg, or any dosage in between. In other embodiments, the total dosage of the compound of formula (I) or the pharmaceutically acceptable salt thereof administered per day is about 500 mg, 600 mg, 700 mg, 800 mg, 900 mg, 1000 mg, 1250 mg, 1500 mg, 1750 mg, or 2000 mg, or any dosage in between.

In certain embodiments, the pharmaceutical composition is administered once per day. In such embodiments, the total dosage of the compound of formula (I) or the pharmaceutically acceptable salt thereof administered per day is about 500 mg to about 700 mg, or any dosage in between.

In some embodiments, the pharmaceutical composition is administered once per day. In such embodiments, the total dosage of the compound of formula (I) or the pharmaceutically acceptable salt thereof administered per day is about 550 mg to about 650 mg, or any dosage in between.

In certain embodiments, the pharmaceutical composition is administered once per day. In such embodiments, the total dosage of the compound of formula (I) or the pharmaceutically acceptable salt thereof administered per day is about 500 mg to about 600 mg, or any dosage in between.

In certain embodiments, the pharmaceutical composition is administered once per day. In such embodiments, the total dosage of the compound of formula (I) or the pharmaceutically acceptable salt thereof administered per day is about 500 mg.

In certain embodiments, the pharmaceutical composition is administered once per day. In such embodiments, the total dosage of the compound of formula (I) or the pharmaceutically acceptable salt thereof administered per day is about 550 mg.

In certain embodiments, when the pharmaceutical composition is orally administered once per day, the total dosage of the compound of formula (I) or the pharmaceutically acceptable salt thereof administered per administration is about 600 mg.

In one embodiment, the pharmaceutical composition is administered twice per day. In such embodiments, the total dosage of the compound of formula (I) or the pharmaceutically acceptable salt thereof administered per administration is about 50 mg, 75 mg, 100 mg, 150 mg, 200 mg, 250 mg, 300 mg, 400 mg, 500 mg, 600 mg, 700 mg, 800 mg, 900 mg, or 1000 mg, or any dosage in between.

In some embodiments, when the pharmaceutical composition is orally administered twice per day, the total dosage of the compound of formula (I) or the pharmaceutically acceptable salt thereof administered per day is about 200 mg, 300 mg, 400 mg, 500 mg, 600 mg, 700 mg, 800 mg, 900 mg, 1000 mg, 1250 mg, 1500 mg, 1750 mg, or 2000 mg, or any dosage in between. In other embodiments, when the pharmaceutical composition is orally administered twice per day, the total dosage of the compound of formula (I) or the pharmaceutically acceptable salt thereof administered per day is about 500 mg, 600 mg, 700 mg, 800 mg, 900 mg, 1000 mg, 1250 mg, 1500 mg, 1750 mg, or 2000 mg, or any dosage in between.

In certain embodiments, when the pharmaceutical composition is orally administered twice per day, the total dosage of the compound of formula (I), or the pharmaceutically acceptable salt thereof, administered per administration is about 250 mg.

In certain embodiments, when the pharmaceutical composition is orally administered twice per day, the total dosage of the compound of formula (I), or the pharmaceutically acceptable salt thereof, administered per administration is about 275 mg.

In certain embodiments, when the pharmaceutical composition is orally administered twice per day, the total dosage of the compound of formula (I) or the pharmaceutically acceptable salt thereof administered per administration is about 300 mg.

In some embodiments, the pharmaceutically acceptable salt of the compound of formula (I) means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

In some embodiments, the compound of formula (I) is a crystalline form, and the crystalline form can be any form of the compound of formula (I) as described in the invention, or a mixture thereof.

In some embodiments, the administration of the pharmaceutical composition does not result in a serious adverse effect. In certain embodiments, the serious adverse effect is a thromboembolic event, a malignancy, lymphopenia, neutropenia, liver enzyme elevation, lipid elevation, serum creatinine elevation, or a serious infection.

In some embodiments, the administration of the pharmaceutical composition does not result in clinically significant changes from the predose baseline in a laboratory assessment, a vital sign or an electrocardiogram (ECG).

In certain embodiments, the laboratory assessment is selected from the group consisting of lipid, coagulation, hematology and natural killer (NK) cell counts.

In certain embodiments, the vital sign is selected from the group consisting a body temperature, respiratory rate, blood pressure and heart rate.

In certain embodiments, the ECG is safety 12-lead ECGs or Holter monitoring for cardiodynamic assessment.

According to embodiments of the invention, a variety of factors can be analyzed to determine by clinical trials such as those described herein whether a particular dosage of the compound of formula (I) provides for safe oral administration. For example, safety of a certain dosage of orally administered JAK3 inhibitor can be assessed by pharmacokinetic studies (e.g., an area under the concentration time curve (AUC), and a maximum concentration observed ($C_{max}$). The safety of orally administered JAK3 inhibitor can also be monitored by physical examination of the subject; allergic reactions; electrocardiograms; clinical laboratory tests; vital signs; and monitoring of other adverse events.

In some embodiments, clinically proven safe administration of the compound of formula (I) is determined by assessing pharmacokinetic (PK) parameters, such as an area under the concentration time curve (AUC), and a maximum concentration observed ($C_{max}$), of the inhibitor in the plasma of the subject. Plasma samples are analyzed to determine concentrations of the inhibitor by any method known in the art in view of the present disclosure. The pharmacokinetic parameters are then analyzed, for example by non-compartment analysis (NCA), to calculate pharmacokinetic parameters, such as AUC, $C_{max}$, terminal half-life ($T_{1/2}$), total systemic clearance over bioavailability (CL/F), and volume of distribution at terminal phase over bioavailability ($V_z/F$). In particular, AUC can be area under the concentration-time curve from time 0 to the 12 hour time point ($AUC_{0-12}$), area under the concentration-time curve from time 0 to the 24 hour time point ($AUC_{0-24}$), area under the concentration-time curve from time 0 extrapolated to infinity ($AUC_{0-inf}$), area under the concentration-time curve from time 0 to the last observed non-zero concentration (t) ($AUC_{0-t}$), area under the concentration-time curve during a dosing interval (tau) at steady state ($AUC_{0-tau}$), or area under the concentration-time curve from time 0 to the last observed non-zero concentration (t) at steady-state ($AUC_{ss0-t}$).

In some embodiments, the single administration of the pharmaceutical composition in an amount sufficient to provide from about 100 mg to about 2000 mg of the compound of formula (I) or a pharmaceutically acceptable salt thereof achieves, in the plasma of the subject, an area under the concentration time curve from time 0 extrapolated to infinity ($AUC_{0-inf}$) of about 2.70 ng.hr/mL to about 172 ng.hr/mL; including an average $AUC_{0-inf}$ of from about 8.38 ng.hr/mL to about 96.0 ng.hr/mL.

In some embodiments, the repeated administration of the pharmaceutical composition in an amount sufficient to provide from about 100 mg to about 1000 mg twice per day of the compound of formula (I) or a pharmaceutically acceptable salt thereof achieves, in the plasma of the subject, an area under the concentration time curve from time 0 to the 12 hour time point at steady-state ($AUC_{ss0-12}$) of about 5.43 ng.hr/mL to about 88.5 ng.hr/mL including an average $AUC_{ss0-12}$ of from about 8.94 ng.hr/mL to about 62.1 ng.hr/mL.

In some embodiments, the administration of the pharmaceutical composition achieves, in the plasma of the subject, a maximum concentration observed ($C_{max}$) of not more than about 50 μg/mL, preferably not more than 40 μg/mL, more preferably about 35 μg/mL.

In some embodiments, the administration of the pharmaceutical composition achieves, in the plasma of the subject, a maximum concentration observed ($C_{max}$) of not more than about 50 ng/mL, preferably not more than 40 ng/mL, more preferably about 35 ng/mL.

In some embodiments, the pharmaceutical composition is orally administered twice per day and achieves a steady-state condition of the compound of formula (I) within 8 days, preferably 7 days, after the second administration when the total dosage per administration is about 50 mg, 100 mg, 150 mg, or any dosage in between.

In some embodiments, the pharmaceutical composition is orally administered twice per day and achieves a steady-state condition of the compound of formula (I) within 8 days, preferably 3 days, after the second administration when the total dosage per administration is 300 mg, 400 mg, 500 mg, 600 mg, 700 mg, 800 mg, 900 mg, 1000 mg, or any dosage in between.

In some embodiments, the repeat administration of the pharmaceutical composition in an amount sufficient to provide from about 100 mg to about 1000 mg twice per day of the compound of formula (I) or a pharmaceutically acceptable salt thereof achieves a maximum observed concentration at steady-state ($C_{max,ss}$ (of not more than about 25 ng/mL, preferably 13 ng/ml.

In some embodiments, the administration of the pharmaceutical composition achieves a mean terminal elimination half-life of about 11 to 30 hours, including about 15 to 20 hours.

In some embodiments, the pharmaceutical composition is orally administered once per day and achieves a urinary excretion of the compound formula (I) of not more than including not more than 0.5%, such as not more than 0.1%.

In some embodiments, the human subject is in need of a treatment of a gastrointestinal inflammatory disease. In certain embodiments, the gastrointestinal inflammatory disease is immune checkpoint inhibitor induced colitis, CTLA-4 inhibitor-induced colitis, graft versus host disease-related colitis, celiac disease, collagenous colitis, lymphocytic colitis, Behcet's disease, ileitis, eosinophilic esophagitis, or infectious colitis.

In another general aspect, the invention relates to a method of treating a gastrointestinal inflammatory disease in a human subject in need thereof, the method comprising orally administering to the subject a compound of formula (I):

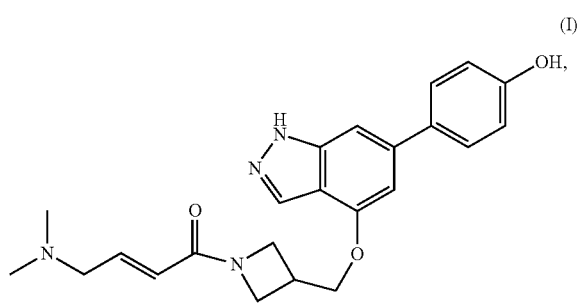 [SMILES: CN(C)C/C=C/C(=O)N1CC(COc2cc(-c3ccc(O)cc3)cc3[nH]ncc23)C1]

or a pharmaceutically acceptable salt thereof, wherein the compound of formula (I), or the pharmaceutically acceptable salt thereof, is administered to the subject in an amount sufficient to provide from about 500 mg per day to about 2000 mg per day of the compound of formula (I) or a pharmaceutically acceptable salt thereof.

In another general aspect, the invention relates to a method of treating a gastrointestinal inflammatory disease in a human subject in need thereof, the method comprising orally administering to the subject a pharmaceutical composition comprising a pharmaceutically acceptable carrier and a compound of formula (I):

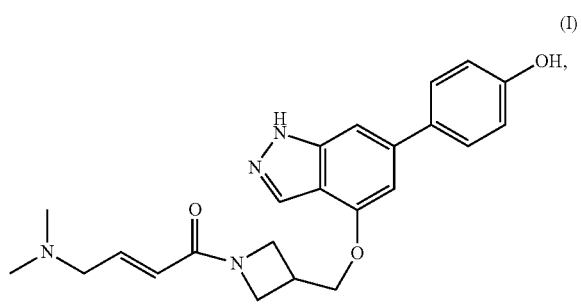 [SMILES: CN(C)C/C=C/C(=O)N1CC(COc2cc(-c3ccc(O)cc3)cc3[nH]ncc23)C1]

or a pharmaceutically acceptable salt thereof, wherein the pharmaceutical composition is administered to the subject in an amount sufficient to provide from about 500 mg per day to about 2000 mg per day of the compound of formula (I) or a pharmaceutically acceptable salt thereof.

In another general aspect, the invention relates to a compound of formula (I):

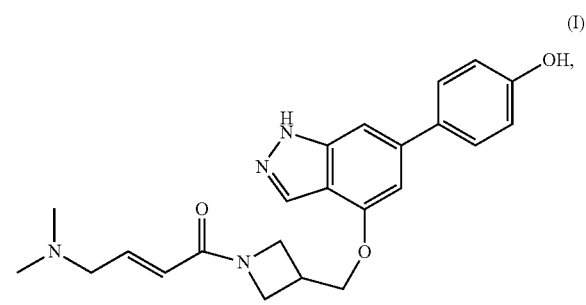 [SMILES: CN(C)C/C=C/C(=O)N1CC(COc2cc(-c3ccc(O)cc3)cc3[nH]ncc23)C1]

or a pharmaceutically acceptable salt thereof, for use in the treatment of a gastrointestinal inflammatory disease in a human subject, wherein the compound of formula (I), or the pharmaceutically acceptable salt thereof, is orally administered to the subject in an amount sufficient to provide from about 500 mg per day to about 2000 mg per day of the compound of formula (I) or a pharmaceutically acceptable salt thereof.

In another general aspect, the invention relates to a pharmaceutical composition comprising a pharmaceutically acceptable carrier and a compound of formula (I):

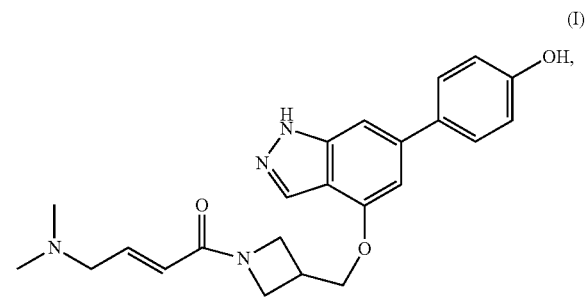 [SMILES: CN(C)C/C=C/C(=O)N1CC(COc2cc(-c3ccc(O)cc3)cc3[nH]ncc23)C1]

or a pharmaceutically acceptable salt thereof, for use in the treatment of a gastrointestinal inflammatory disease in a human subject, wherein the composition is orally administered to the subject in an amount sufficient to provide from about 500 mg per day to about 2000 mg per day of the compound of formula (I) or a pharmaceutically acceptable salt thereof.

In another general aspect, the invention relates to use of a compound of formula (I):

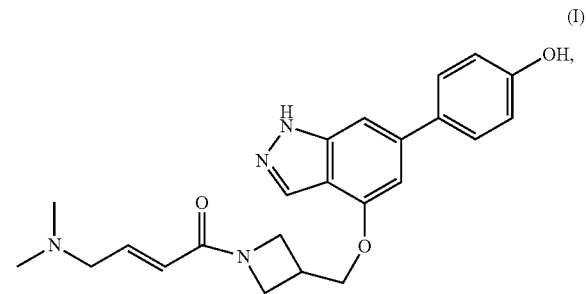 [SMILES: CN(C)C/C=C/C(=O)N1CC(COc2cc(-c3ccc(O)cc3)cc3[nH]ncc23)C1]

or a pharmaceutically acceptable salt thereof, in the manufacture of a medicament for the treatment of a gastrointestinal inflammatory disease in a human subject, wherein the compound of formula (I), or the pharmaceutically acceptable salt thereof, is orally administered to the subject in an amount sufficient to provide from about 500 mg per day to about 2000 mg per day of the compound of formula (I) or a pharmaceutically acceptable salt thereof.

In another general aspect, the invention relates to use of a pharmaceutical composition comprising a pharmaceutically acceptable carrier and a compound of formula (I):

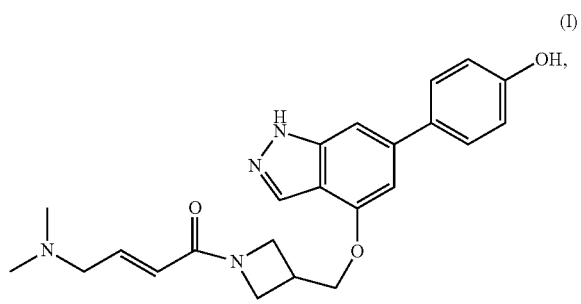 [SMILES: CN(C)C/C=C/C(=O)N1CC(COc2cc(-c3ccc(O)cc3)cc3[nH]ncc23)C1]

(I)

or a pharmaceutically acceptable salt thereof, in the manufacture of a medicament for the treatment of a gastrointestinal inflammatory disease in a human subject, wherein the pharmaceutical composition is orally administered to the subject in an amount sufficient to provide from about 500 mg per day to about 2000 mg per day of the compound of formula (I) or a pharmaceutically acceptable salt thereof.

The following embodiments apply to each of the general aspects disclosed herein, including the above-described general aspects.

In some embodiments, the gastrointestinal inflammatory disease is immune checkpoint inhibitor induced colitis, CTLA-4 inhibitor-induced colitis, graft versus host disease-related colitis, celiac disease, collagenous colitis, lymphocytic colitis, Behcet's disease, ileitis, eosinophilic esophagitis, or infectious colitis. In a particular embodiment, the gastrointestinal inflammatory disease is celiac disease.

In one embodiment, the compound of formula (I) or a pharmaceutically acceptable salt thereof is administered once per day. In such embodiments, the compound of formula (I) or a pharmaceutically acceptable salt thereof is administered to the subject in an amount sufficient to provide about 500 mg per day to 1000 mg per day, for example, 500 mg per day, 600 mg per day, 700 mg per day, 800 mg per day, 900 mg per day, or 1000 mg per day of the compound of formula (I) or a pharmaceutically acceptable salt.

In one embodiment, the pharmaceutical composition is administered once per day. In such embodiments, the pharmaceutical composition is administered to the subject in an amount sufficient to provide about 500 mg per day to 1000 mg per day, for example, 500 mg per day, 600 mg per day, 700 mg per day, 800 mg per day, 900 mg per day, or 1000 mg per day of the compound of formula (I) or a pharmaceutically acceptable salt.

In one embodiment, the compound of formula (I) or a pharmaceutically acceptable salt thereof is administered twice per day. In such embodiments, the compound of formula (I) or a pharmaceutically acceptable salt thereof is administered to the subject in an amount sufficient to provide about 500 mg per day to 1000 mg per day, for example, 500 mg per day, 600 mg per day, 700 mg per day, 800 mg per day, 900 mg per day, or 1000 mg per day of the compound of formula (I) or a pharmaceutically acceptable salt.

In one embodiment, the pharmaceutical composition is administered twice per day. In such embodiments, the pharmaceutical composition is administered to the subject twice per day in an amount sufficient to provide about 600 mg per day of the compound of formula (I) or a pharmaceutically acceptable salt.

In some embodiments, the compound of formula (I) is present in a crystalline form, and the crystalline form can be any form of the compound of formula (I) as described in the invention, or a mixture thereof.

Crystalline Forms

According to the embodiments of the invention, the crystalline form of the compound of formula (I) can be Form 3 or Form 4, as described below.

Form 3

Crystalline Form 3 of the invention is a crystalline anhydrous free form of the compound of formula (I). In one aspect, Form 3 is characterized by a powder X-ray diffraction (PXRD) pattern having significant diffraction peaks, among other peaks, at 2θ values of 9.67±0.20, 11.61±0.20, 17.61±0.20, 18.88±0.20, and 23.33±0.20. Form 3 can be further characterized by a PXRD pattern having additional diffraction peaks at 2θ values of 4.82±0.20, 15.69±0.20, and 16.19±0.20. Form 3 can be further characterized by a PXRD pattern having two or more additional diffraction peaks, including three or more and four or more additional diffraction peaks at 2θ values selected from 11.92±0.20, 12.98±0.20, 13.23±0.20, 16.45±0.20, 16.67±0.20, 19.39±0.20, 19.96±0.20, 20.14±0.20, 22.14±0.20, 23.84±0.20, 24.06±0.20, 24.29±0.20, 25.31±0.20, 25.63±0.20, 27.06±0.20, 27.31±0.20, 30.10±0.20, and 30.53±0.20. Form 3 is characterized by a PXRD pattern having three, four, five, or six diffraction peaks at 2θ values selected from 4.82±0.20, 9.67±0.20, 11.61±0.20, 15.69±0.20, 16.19±0.20, 17.61±0.20, 18.88±0.20, and 23.33±0.20.

Figure 2:
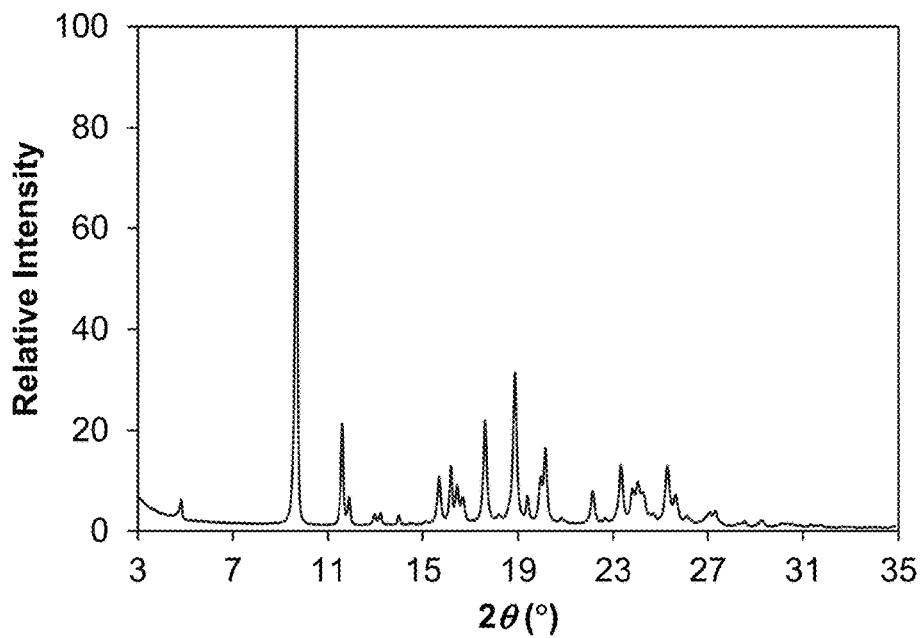
FIG. 2 shows a powder x-ray diffraction (PXRD) pattern of crystalline Form 3 of the compound of formula (I) (hereinafter Form 3).

As is well known in the field of powder X-ray diffraction, peak positions of PXRD pattern are relatively less sensitive to experimental details, such as details of sample preparation and instrument geometry, than are the relative peak heights. Thus, in one aspect, the crystalline Form 3 is characterized by a powder x-ray diffraction pattern in which the peak positions are substantially in accordance with those shown in FIG. 2.

Figure 3:
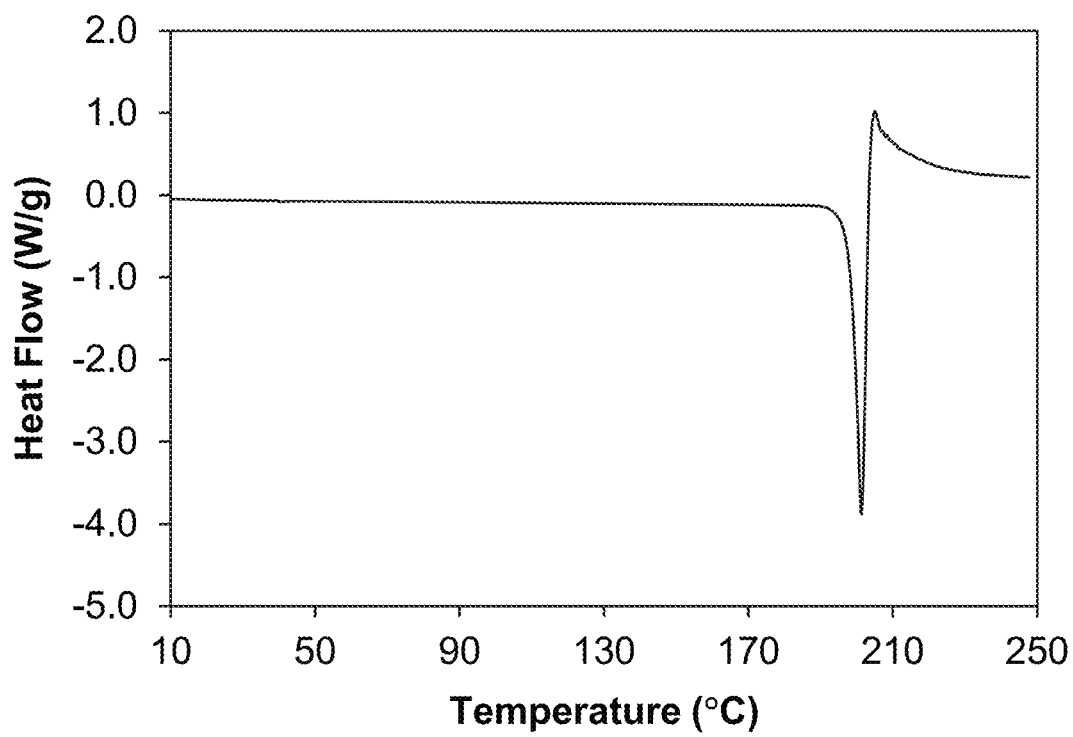
FIG. 3 shows a differential scanning calorimetry (DSC) thermogram of crystalline Form 3.

In another aspect, crystalline Form 3 is characterized by its behavior when exposed to high temperature. As demonstrated in FIG. 3, the differential scanning calorimetry (DSC) trace recorded at a heating rate of 10° C. per minute exhibits a peak in endothermic heat flow, identified as a melt transition, with an onset at about 197.7° C. and a peak at about 201.3° C. Melting was followed immediately by decomposition.

The crystalline form is characterized by a differential scanning calorimetry trace recorded at a heating rate of 10° C. per minute which shows a maximum in endothermic heat flow with a peak at 201.3° C.±2° C.

The crystalline form is characterized by a differential scanning calorimetry trace recorded at a heating rate of 10° C. per minute which shows a maximum in endothermic heat flow at a temperature between 198° C. and 204° C.

Figure 4:
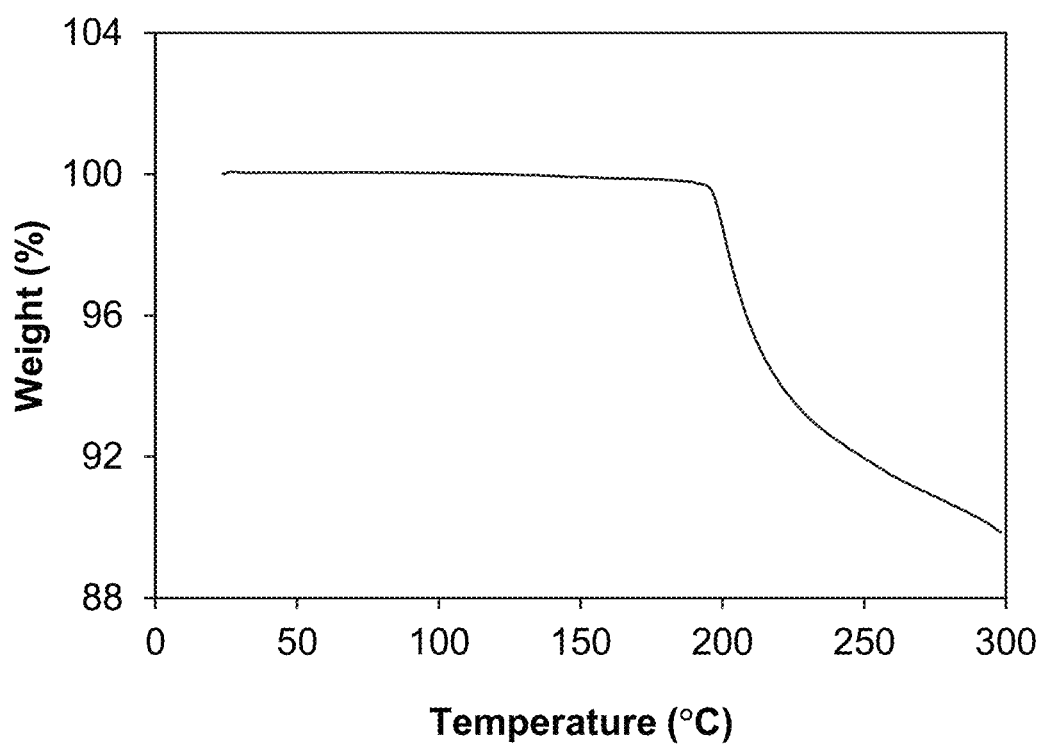
FIG. 4 shows a thermal gravimetric analysis (TGA) plot of crystalline Form 3.

A representative TGA trace of the Form 3 crystalline free form of the invention is shown in FIG. 4. The thermal gravimetric analysis (TGA) trace of FIG. 4 shows no significant weight loss at temperatures below the onset of decomposition at about 195° C.

Figure 5:
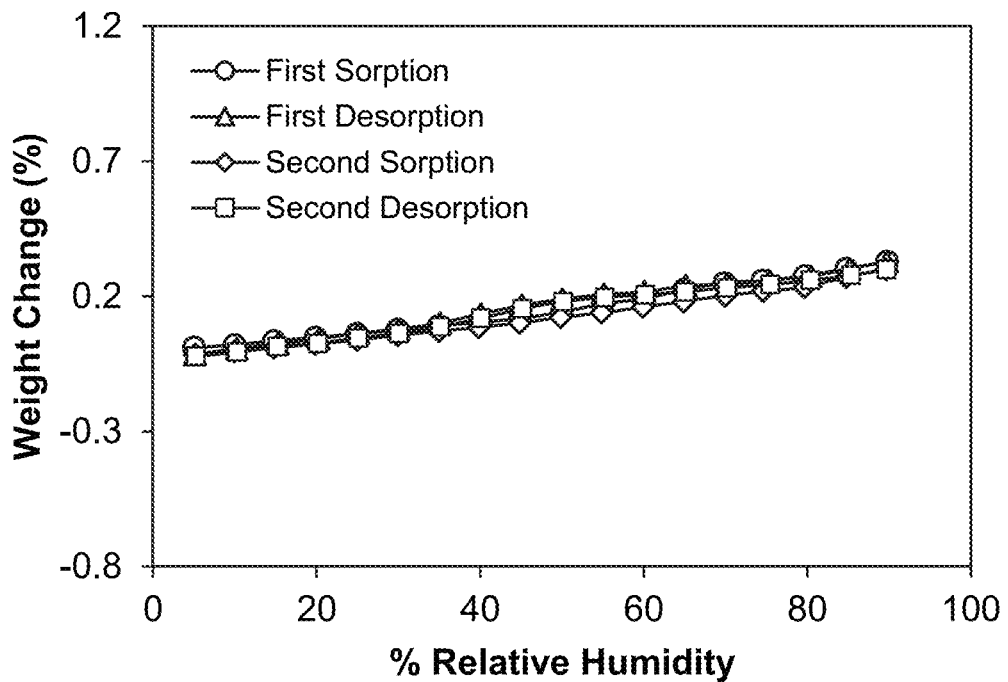
FIG. 5 shows a dynamic moisture sorption (DMS) isotherm of crystalline Form 3 observed at a temperature of about 25° C.

A representative DMS trace for the Form 3 crystalline free form of the invention is shown in FIG. 5. Form 3 demonstrated about 0.33% weight gain in the humidity range of 5% to 90% relative humidity. Form 3 is considered to be non-hygroscopic.

Form 3 can be prepared by suspending the compound of formula (I) in an amorphous form in a 1:1 mixture of acetonitrile and isopropanol. The resulting suspension is stirred for about 1 day at about 50° C., filtered, optionally washed with a 1:1 mixture of acetonitrile and isopropanol and dried for a few hours to provide Form 3.

Form 3 can be prepared by dissolving the compound of formula (I) as an amorphous free base in IPA at a temperature of between about 20° C. and about 25° C. An equal amount of acetonitrile is added. More amounts of the compound can be added until a saturated solution is formed. Seeds are added and the mixture is stirred overnight. The developing white slurry formed is filtered and dried to yield Form 3.

Form 4

Crystalline Form 4 of the invention is a crystalline hydrate free form of the compound of formula (I). In one aspect, Form 4 is characterized by a powder X-ray diffraction (PXRD) pattern having significant diffraction peaks, among other peaks, at 2θ values of 6.26±0.20, 16.55±0.20, 16.94±0.20, 18.33±0.20, 23.61±0.20, and 24.24±0.20. Form 4 can be further characterized by a PXRD pattern having additional diffraction peaks at 2θ values of 11.86±0.20, 12.51±0.20, 13.16±0.20, and 14.98±0.20. Form 4 can be further characterized by a PXRD pattern having two or more additional diffraction peaks, including three or more and four or more additional diffraction peaks at 2θ values selected from 17.61±0.20, 18.78±0.20, 19.39±0.20, 19.57±0.20, 19.84±0.20, 21.45±0.20, 21.82±0.20, 22.57±0.20, 24.67±0.20, 25.10±0.20, 25.39±0.20, 27.19±0.20, 27.39±0.20, 28.55±0.20, and 31.51±0.20. Form 4 is characterized by a PXRD pattern having three, four, five, or six diffraction peaks at 2θ values selected from 6.26±0.20, 11.86±0.20, 12.51±0.20, 13.16±0.20, 14.98±0.20, 16.55±0.20, 16.94±0.20, 18.33±0.20, 23.61±0.20, and 24.24±0.20.

Figure 6:
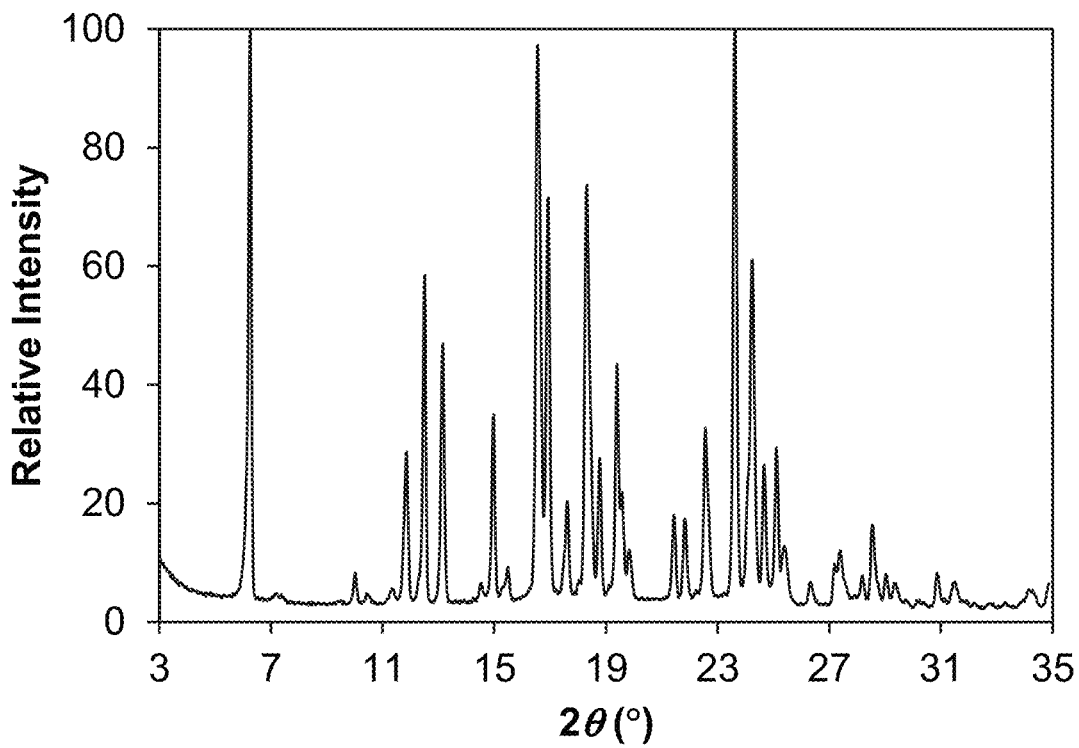
FIG. 6 shows a powder x-ray diffraction (PXRD) pattern of crystalline Form 4 of the compound of formula (I) (hereinafter Form 4).

As is well known in the field of powder X-ray diffraction, peak positions of PXRD pattern are relatively less sensitive to experimental details, such as details of sample preparation and instrument geometry, than are the relative peak heights. Thus, in one aspect, the crystalline Form 4 is characterized by a powder x-ray diffraction pattern in which the peak positions are substantially in accordance with those shown in FIG. 6.

Figure 7:
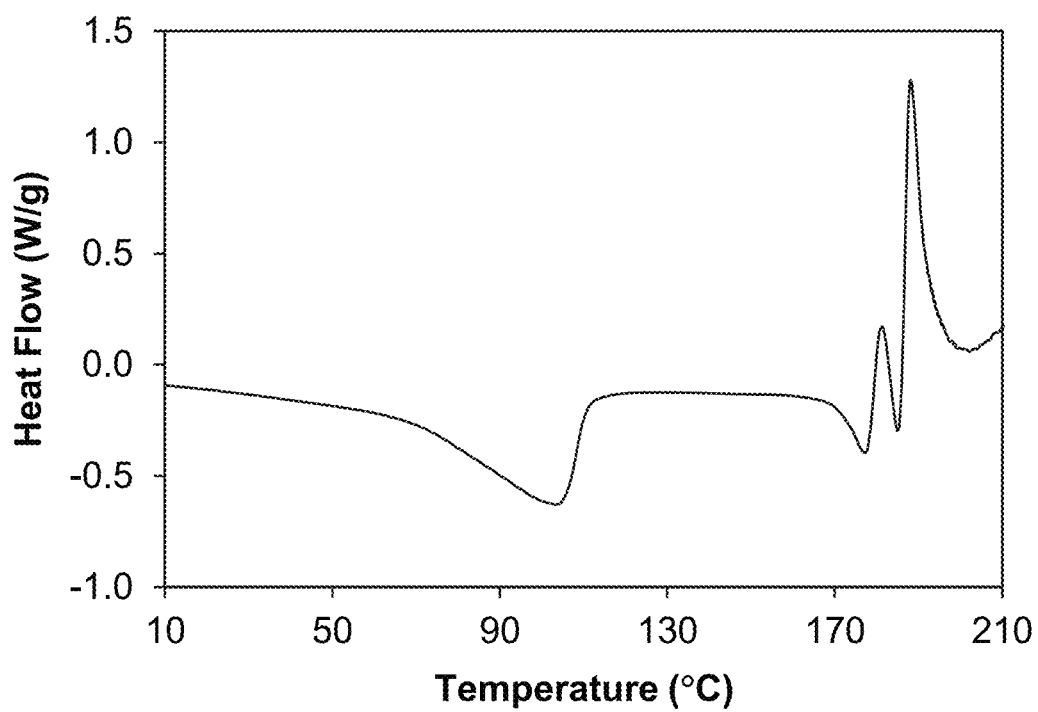
FIG. 7 shows a differential scanning calorimetry (DSC) thermogram of crystalline Form 4.

In another aspect, crystalline Form 4 is characterized by its behavior when exposed to high temperature. As demonstrated in FIG. 7, the differential scanning calorimetry (DSC) trace recorded at a heating rate of 10° C. per minute exhibits a desolvation endotherm with an onset at about 60.9° C. and a peak at about 103.6° C., and a melting endotherm characterized by an onset at about 167.3° C. The compound decomposes at melting and the melting endotherm and the decomposition exotherm overlap.

Figure 8:
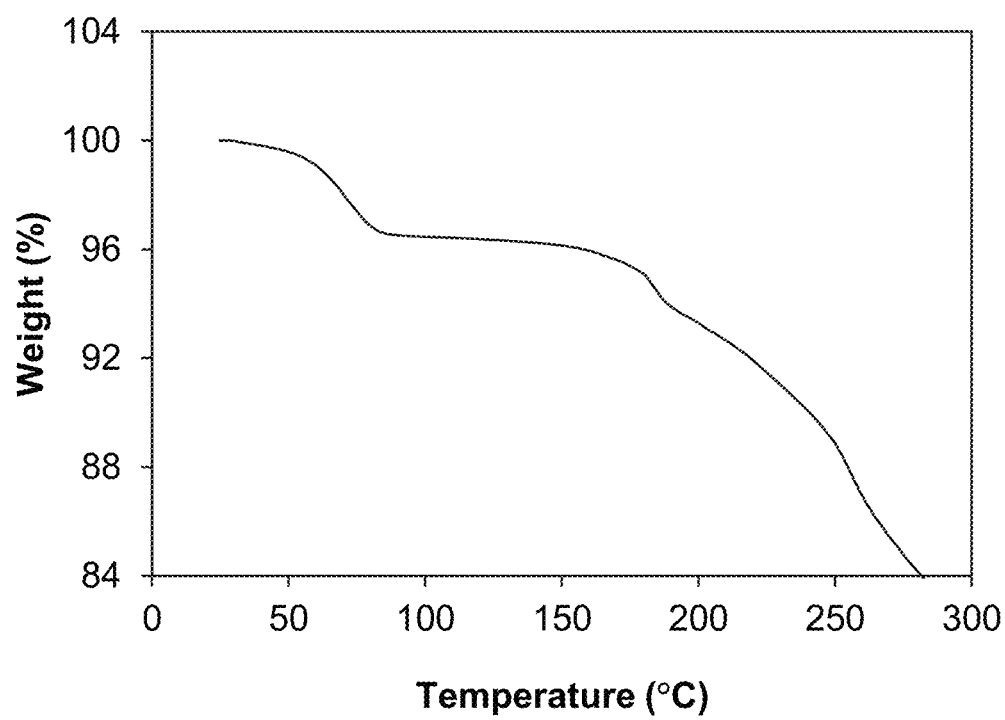
FIG. 8 shows a thermal gravimetric analysis (TGA) plot of crystalline Form 4.

A representative TGA trace of the Form 4 crystalline free form of the invention is shown in FIG. 8. The thermal gravimetric analysis (TGA) trace of FIG. 8 shows a weight loss of about 3.54% at 100° C. The compound desolvates at an onset temperature of about 50° C. The compound decomposes at an onset temperature of about 165° C.

A representative DMS trace for the Form 4 crystalline free form of the invention is shown in FIG. 9. Form 4 demonstrated about 5.01% weight gain in the humidity range of 5% to 90% relative humidity. Form 4 is considered to be moderately hygroscopic.

Form 4 can be prepared by suspending the compound of formula (I) in water. The resulting suspension is stirred for about 1 to 2 days at about 50° C., filtered, optionally washed with water, and dried at a temperature of between about 20° C. and about 25° C. for about 2-6 hours to provide Form 4.

Alternatively, Form 4 can be prepared by dissolving the compound of formula (I) in ethanol and water or methanol and water by complete dissolution in about 10 volumes of alcohol followed by slow addition of about 8-10 volumes of water until cloud point. Seeds of Form 4 are added and resulting slurry develops slowly over time. Then more water is added slowly (about 10 volumes) and the solid is filtered and dried to give Form 4.

Pharmaceutical Compositions

According to the embodiments of the invention, the pharmaceutical composition of the invention typically contains a therapeutically effective amount of the compound of formula (I).

Those skilled in the art will recognize, however, that a pharmaceutical composition can contain more than a therapeutically effective amount, e.g., bulk compositions, or less than a therapeutically effective amount, e. g., individual unit doses designed for multiple administration to achieve a therapeutically effective amount.

Typically, such pharmaceutical compositions will contain from about 0.1% to about 95% by weight of the compound of formula (I); including from about 5% to about 70% by weight of the compound of formula (I).

The pharmaceutical composition of the invention comprises a pharmaceutically acceptable carrier, such as those widely employed in the art of drug manufacturing. As used herein, the term "carrier" refers to any excipient, diluent, buffer, stabilizer, or other material well known in the art for pharmaceutical formulations. Pharmaceutically acceptable carriers in particular are non-toxic and should not interfere with the efficacy of the active ingredient. The pharmaceutically acceptable carriers include excipients and/or additives suitable for use in the pharmaceutical compositions known in the art, e.g., as listed in "Remington: The Science & Practice of Pharmacy", 19th ed., Williams & Williams, (1995), and in the "Physician's Desk Reference", 52nd ed., Medical Economics, Montvale, N.J. (1998), the disclosures of which are entirely incorporated herein by reference. Any conventional carrier or excipient may be used in the pharmaceutical compositions of the invention.

The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the disclosure are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

According to the embodiments of the invention, suitable pharmaceutical compositions for oral administration can be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present disclosure as an active ingredient.

When intended for oral administration in a solid dosage form (e.g., as capsules, tablets, pills and the like), the pharmaceutical compositions will typically comprise the active agent (the compound of formula (I)) and one or more pharmaceutically-acceptable carriers. Optionally, such solid dosage forms may comprise: fillers or extenders, such as starches, microcrystalline cellulose, lactose, dicalcium phosphate, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as crosscarmellose sodium, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the disclosure. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid, methacrylic acid ester copolymers, cellulose acetate trimellitate, carboxymethyl ethyl cellulose, hydroxypropyl methyl cellulose acetate succinate, and the like.

Pharmaceutical compositions of the invention can also be formulated to provide slow or controlled release of the active agent using, by way of example, hydroxypropyl methylcellulose in varying proportions; or other polymer matrices, liposomes and/or microspheres. In addition, the pharmaceutical compositions of the invention can optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), oleic acid, glycerol, tetrahydrofuryl alcohol, polyethylene glycols and fatty acid esters of sorbitan, and mixtures thereof. Alternatively, certain liquid formulations can be converted, for example, by spray drying, to a powder, which is used to prepare solid dosage forms by conventional procedures.

Suspensions, in addition to the active ingredient, can contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The following non-limiting examples illustrate representative pharmaceutical compositions of the present invention.

Tablet Oral Solid Dosage Form A compound of formula (I) or a pharmaceutically-acceptable salt thereof is dry blended with microcrystalline cellulose, polyvinyl pyrrolidone, and crosscarmellose sodium in a ratio of 4:5:1:1 and compressed into tablets to provide a unit dosage of, for example, 10 mg, 20 mg, 40 mg, 60 mg, 80 mg, or 100 mg active agent per tablet.

Capsule Oral Solid Dosage Form

A compound of formula (I) or a pharmaceutically-acceptable salt thereof is combined with microcrystalline cellulose, polyvinyl pyrrolidone, and crosscarmellose sodium in a ratio of 4:5:1:1 by wet granulation and loaded into gelatin or hydroxypropyl methylcellulose capsules to provide a unit dosage of, for example, 10 mg, 20 mg, 40 mg, 60 mg, 80 mg, or 100 mg active agent per capsule.

Liquid Formulation

A liquid formulation comprising a compound of formula (I) (0.1%), water (98.9%) and ascorbic acid (1.0%) is formed by adding a compound of the disclosure to a mixture of water and ascorbic acid.

Enteric Coated Oral Dosage Form

A compound of formula (I) is dissolved in an aqueous solution containing polyvinyl pyrrolidone and spray coated onto microcrystalline cellulose or sugar beads in a ratio of 1:5 w/w active agent:beads and then an approximately 5% weight gain of an enteric coating comprising an acrylic copolymer, for example a combination of acrylic copolymers available under the trade names Eudragit-L® and Eudragit-S®, or hydroxypropyl methylcellulose acetate succinate is applied. The enteric coated beads are loaded into gelatin or hydroxypropyl methylcellulose capsules to provide a unit dosage of, for example, 10 mg, 20 mg, 40 mg, 60 mg, 80 mg, or 100 mg active agent per capsule.

Enteric Coated Oral Dosage Form

An enteric coating comprising a combination of Eudragit-L® and Eudragit-S®, or hydroxypropyl methylcellulose acetate succinate is applied to a tablet oral dosage form or a capsule oral dosage form described above.

Utility

Inhibition of JAK3 blocks the signaling of many key pro-inflammatory cytokines. Thus, the compound of formula (I) is expected to be useful in the treatment of inflammatory diseases.

The compound of formula (I) has been designed to be selective for JAK3 over JAK1, JAK2 and TYK2. Selectivity for JAK3 over JAK1 is anticipated to be beneficial as there is some evidence that JAK3 selectivity allows sparing of potentially beneficial cytokines such as IL-10 which has been involved in mucosal healing, IL-22 which is involved in mucus barrier protection and epithelial regeneration, and IL-6 which is involved in the proliferation of intestinal epithelial cells. Selectivity for JAK3 over JAK2 allows sparing of erythropoietin (EPO) and thrombopoietin (TPO) signaling.

Without being limited by this theory, the compound of formula (I) possesses an electrophilic portion which can form a covalent bond with the cysteine (Cys909) present in JAK3, a residue replaced by a serine in the other three JAK isoforms (Goedken et al., *J Biol Chem.,* 2015, 290, 8, 4573-89). Such covalent binding to JAK3 could be beneficial by providing an extended target engagement which may translate in better efficacy. As described in the experimental part, co-crystal structures of the compound of formula (I) covalently bound to human JAK3 have been obtained which confirms the irreversible binding nature for each of these ligands to JAK3.

The compound of formula (I) has also been designed to be gut selective by having limited oral absorption and rapid systemic clearance to avoid or minimize the potential for systemic adverse events, thereby avoiding the potential adverse systemic immunosuppressive effects.

Gastrointestinal Inflammatory Disease

In addition to providing potent inhibition of JAK3, the compound of formula (I) has been designed to be poorly absorbed to minimize systemic exposure. It is designed to have the effect at the site of action, for example, in the colon.

In a Caco-2 permeation assay which was performed to model the ability of test compounds to pass through the intestine and get into the blood stream after oral administration, the compound of formula (I) exhibited low permeabilities with $K_p$ values less than about $5 \times 10^{-6}$ cm/sec which is considered favorable to minimize systemic exposure and target the colon. In a study on the colon and plasma mouse pharmacokinetics, the compound of formula (I) exhibited a $K_p$ value less than about $10 \times 10^{-6}$ cm/sec which can also be sufficient to minimize systemic exposure and target the colon, and the compound of formula (I) exhibited a ratio of exposure in the colon to exposure in plasma upon oral administration greater than about 1250.

Oxazolone-induced colitis is an experimental model that has a histological resemblance to human ulcerative colitis. The compound of formula (I) demonstrated activity in the oxazolone-induced colitis model in mice. Further, when tested in an immunosuppression model in mice, which probes systemic functional activity, splenic NK cell counts were unaffected by the compound of formula (I) at the same or higher doses required to demonstrate efficacy in the above oxazolone model.

Therefore, the compound of formula (I) has been shown to demonstrate lack of systemic activity in a murine model of IL-2 induced pSTAT5 induction in the thymus. Thus, the compound of formula (I) demonstrated anti-colitic activity without exhibiting systemic effects in preclinical models.

It is expected that a high colon to plasma ratio will provide robust, luminally-driven anti-inflammatory activity without associated, systemically-driven, adverse effects. Such compound is useful for a variety of gastrointestinal inflammatory indications that include, but are not limited to, inflammatory bowel disease, ulcerative colitis (proctosigmoiditis, pancolitis, ulcerative proctitis and left-sided colitis), Crohn's disease, collagenous colitis, lymphocytic colitis, Behcet's disease, celiac disease, immune checkpoint inhibitor induced colitis, ileitis, eosinophilic esophagitis, graft versus host disease-related colitis, and infectious colitis. Ulcerative colitis (Reimund et al., *J Clin Immunology,* 1996, 16, 144-150), Crohn's disease (Woywodt et al., *Eur J Gastroenterology Hepatology,* 1999, 11, 267-276), collagenous colitis (Kumawat et al., *Mol Immunology,* 2013, 55, 355-364), lymphocytic colitis (Kumawat et al., 2013), eosinophilic esophagitis (Weinbrand-Goichberg et al., *Immunol Res,* 2013, 56, 249-260), graft versus host disease-related colitis (Coghill et al., *Blood,* 2001, 117, 3268-3276), infectious colitis (Stallmach et al., *Int J Colorectal Dis,* 2004, 19, 308-315), Behcet's disease (Zhou et al., *Autoimmun Rev,* 2012, 11, 699-704), celiac disease (de Nitto et al., *World J Gastroenterol,* 2009, 15, 4609-4614), immune checkpoint inhibitor induced colitis (e.g., CTLA-4 inhibitor-induced colitis; (Yano et al., *J Translation Med,* 2014, 12, 191), PD-1- or PD-L1-inhibitor-induced colitis), and ileitis (Yamamoto et al., *Dig Liver Dis,* 2008, 40, 253-259) are characterized by elevation of certain pro-inflammatory cytokine levels. As many pro-inflammatory cytokines signal via JAK activation, the compound of formula (I) described in this application may be able to alleviate the inflammation and provide symptom relief.

In particular, the compound of formula (I) can be useful for the induction and maintenance of remission of ulcerative colitis, and for the treatment of Crohn's disease, celiac disease, immune checkpoint inhibitor induced colitis, and the gastrointestinal adverse effects in graft versus host disease.

Combination Therapy

The pharmaceutical composition of the invention can also be used in combination with one or more agents which act by the same mechanism or by different mechanisms to effect treatment of gastrointestinal inflammatory disorders. The different agents can be administered sequentially or simultaneously (in separate compositions or in the same composition). Useful classes of agents for combination therapy include, but are not limited to, aminosalicylates, steroids, systemic immunosuppressants, anti-TNFα antibodies, TNF alpha ligand inhibitor, TNF binding agent, anti-VLA-4 antibodies, anti-integrin $\alpha_4\beta_7$ antibodies, anti-bacterial agents, Glucocorticoid agonists, Nuclear factor kappa B inhibitors, 5-Lipoxygenase inhibitors, integrin alpha-4/beta-7 antagonist, Cyclooxygenase inhibitors, IL-23 antagonists, Leukotriene BLT receptor antagonist, IL-6 antagonists, IL-8 antagonists, integrin antagonists, nicotinic acetylcholine receptor agonists, PPAR gamma agonists, sphingosine-1-phosphate receptor-1 modulators, B-lymphocyte antigen CD20 inhibitors, calcineurin inhibitors, CD3 antagonist, cell adhesion molecule inhibitors, eosinophil peroxidase inhibitors, heparin agonists, ICAM1 gene inhibitors, IL-13 antagonists, IL-2 receptor alpha subunit inhibitors, insulin sensitizers, interferon beta ligands, interferon gamma receptor antagonists, interleukin-1 beta ligand modulators, MAdCAM inhibitors, PDE 4 inhibitors, sphingosine-1-phosphate receptor-1 agonists, TLR-9 agonists, acetylcholinesterase inhibitors, ACTH receptor agonists, activin receptor antagonists, CCR5 chemokine antagonists, CCR9 chemokine antagonists, and anti-diarrheal medicines.

Aminosalicylates that can be used in combination include, but are not limited to, mesalamine, osalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNFα antibodies, which include, but are not limited to, infliximab, adalimumab, golimumab, and certolizumab, may be used in combination therapy. Useful compounds acting by other mechanisms include anti-VLA-4 antibodies, such as natalizumab, anti-integrin $\alpha_4\beta_7$ antibodies, such as vedolizumab, anti-bacterial agents, such as rifaximin, and anti-diarrheal medicines, such as loperamide (Mozaffari et al. *Expert Opin. Biol. Ther.* 2014, 14, 583-600; Danese, *Gut*, 2012, 61, 918-932; Lam et al., *Immunotherapy*, 2014, 6, 963-971).

Other compounds that can be used in combination include, but are not limited to opaganib, abatacept, mongersen, filgotinib, LYC-30937, BI-655130, mirikizumab, adalimumab, tacrolimus, rituximab, GSK-2982772, andecaliximab, naltrexone, risankizumab, QBECO, alicaforsen, etrolizumab, foralumab, ocrelizumab, vedolizumab, amiselimod, ozanimod, dolcanatide, catridecacog, budesonide, STNM-01, cannabidiol, telotristat etiprate, SHP-647, carotegrast methyl, peg-ilodecakin, TOP-1288, iberogast N, PF-06480605, peficitinib, beclomethasone, recombinant interferon beta-1a, infliximab, golimumab, tralokinumab, ustekinumab, certolizumab pegol, thalidomide, upadacitinib, apremilast, natalizumab, interferon beta-1a, rifaximin, RBX-2660, etrasimod, zileuton, fingolimod, cobitolimod, ropivacaine, ABX-464, PF-06700841, prednisolone, GLPG-0974, valganciclovir, ciclosporin, VB-201, tulinercept, MDGN-002, PTG-100, dexamethasone, GED-0507-34-Levo, bertilimumab, brazikumab, KHK-4083, rosiglitazone, mocravimod, sotrastaurin, KAG-308, PUR-0110, E-6007, balsalazide, basiliximab, LP-02, ASP-3291, Trichuris suis ova, K(D)PT, midismase, DNVX-078, vatelizumab, alequel, low molecular weight heparin, metenkefalin, tridecactide, HMPL-004, SB-012, olsalazine, balsalazide, propionyl-L-carnitine, Clostridium butyricum, beclomethasone and acemannan.

In another aspect, therefore, the invention provides a therapeutic combination for use in the treatment of gastrointestinal inflammatory disorders, the combination comprising the compound of formula (I), or the pharmaceutically acceptable salt thereof, and one or more other therapeutic agents useful for treating gastrointestinal inflammatory disorders, such as the ones illustrated above. For example, the invention provides a combination comprising the compound of formula (I), or the pharmaceutically acceptable salt thereof, and one or more agents selected from aminosalicylates, steroids, systemic immunosuppressants, anti-TNFα antibodies, anti-VLA-4 antibodies, anti-integrin $\alpha_4\beta_7$ antibodies, anti-bacterial agents, and anti-diarrheal medicines. Secondary agent(s), when included, are present in a therapeutically effective amount, e.g., in any amount that produces a therapeutically beneficial effect when co-administered.

Also provided, therefore, is a pharmaceutical composition comprising the compound of formula (I), or the pharmaceutically acceptable salt thereof, or the crystalline form thereof, and one or more other therapeutic agents useful for treating gastrointestinal inflammatory disorders.

Further, in a method aspect, the invention provides a method of treating gastrointestinal inflammatory disorders, the method comprising administering to the subject the compound of formula (I), or the pharmaceutically acceptable salt thereof, or the crystalline form thereof, and one or more other therapeutic agents useful for treating gastrointestinal inflammatory disorders.

When used in combination therapy, the agents can be formulated in a single pharmaceutical composition, as disclosed above, or the agents can be provided in separate compositions that are administered simultaneously or at separate times, by the same or by different routes of administration. When administered separately, the agents are administered sufficiently close in time so as to provide a desired therapeutic effect. Such compositions can be packaged separately or can be packaged together as a kit. The two or more therapeutic agents in the kit can be administered by the same route of administration or by different routes of administration.

EXAMPLES

Example 1

A Phase 1, Randomized, Double-Blinded, Sponsor-Open, 2-part Placebo-Controlled, Single Ascending Dose Study and Multiple Dose Study of a Compound of Formula (I) in Healthy Subjects This clinical study was the first in human study of a compound of formula (I). The purpose of this study was to assess the safety, tolerability and pharmacokinetics (PK) of the compound of formula (I) through single ascending dose administration (Part A) and multiple dose administrations (Part B) in healthy subjects.

Objectives

1) Evaluate the safety and tolerability of single ascending doses (Part A) and of multiple ascending doses (Part B) of the compound of formula (I) in healthy subjects; and 2) Investigate the PK of single ascending doses (Part A) and of multiple ascending doses (Part B) of the compound of formula (I) in healthy subjects.

Endpoints

Safety:

The number and severity of treatment emergent adverse events (TEAE5) following single (Part A) or multiple (Parts B) oral doses of the compound of formula (I) and matching placebo, and changes in safety laboratory assessments, vital signs, and ECGs.

Pharmacokinetics:

The plasma PK parameters of the compound of formula (I) calculated following single (Part A) or multiple (Parts B) oral doses.

Methods and Subjects

Overview of Study Design

This was a 2-part study in healthy subjects. Subjects participated in only one study part and in each study part, and subjects participated in only 1 cohort. A schematic of the study is demonstrated in FIG. 1. Screening of subjects occurred within 28 days prior to (first) dose. For each cohort in Part A and B there are 8 subjects enrolled (6 dosed with the compound of formula (I) and 2 dosed with matching placebo[s]).

Part A—Single Ascending Dose (SAD)

32 healthy, adult male and female subjects were enrolled in Part A. Four cohorts (A1 to A4) of 8 healthy subjects (6 active and 2 placebo) were evaluated.

In each cohort, healthy subjects meeting eligibility criteria were sequentially randomized in a 3:1 ratio to receive either the compound of formula (I) or matching placebo. Study drug was administered orally as a single dose on the morning of Day 1 following an overnight fast of at least 9.5 hours. Subjects were dosed in an upright (i.e., seated or standing) position and remained upright for 5 minutes following dosing prior to performing study procedures which require a posture change. Subjects were to remain fasted, except water, until after the 4-hour post-dose assessments were completed and the 4-hour post dose PK sample was collected. PK sampling for the compound of formula (I) in plasma and urine were taken Day 1 pre-dose and for 72 hours post-dose.

The doses in Part A are as follows:

Cohort A1: 100 mg the compound of formula (I) (1×100-mg capsule, a capsule containing 100 mg of compound of formula (I)) or matching placebo Cohort A2: 300 mg the compound of formula (I) (3×100-mg capsules) or matching placebos Cohort A3: 1000 mg the compound of formula (I) (10×100-mg capsules) or matching placebos Cohort A4: 2000 mg the compound of formula (I) (20×100-mg capsules) or matching placebos Part B—Multiple Ascending Dose (MAD)

24 healthy, adult male and female subjects were enrolled in Part B. Four cohorts (B1 to B3) of 8 healthy subjects (6 active and 2 placebo) were evaluated.

In each cohort, healthy subjects meeting eligibility criteria were sequentially randomized in a 3:1 ratio to receive either the compound of formula (I) or placebo BID, each morning and evening (approximately 12 hours following the morning dose) for 10 consecutive days of dosing, except for Day 10 where subjects were only received a morning dose. Subjects were dosed in an upright (i.e., seated or standing) position and remained upright for 5 minutes after dosing before a posture change for other study procedures, if applicable. Subjects fasted overnight for at least 9.5 hours prior to morning dose on Day 1 and Day 10. Subjects continued the fast for at least 4 hours post morning dose on these days. For all other morning doses and for all evening doses (i.e., Day 1 evening and Days 2 to 9), subjects were required to fast for at least 2 hours prior and for at least 2 hours following the dose.

PK sampling for the compound of formula (I) in plasma was taken Day 1 pre-morning dose and for 12 hours post-dose and Day 10 pre-morning dose and for 72 hours post Day 10 dose. Additional pre morning dose samples were taken on Days 2, 4, 6, and 8.

Dosing occurred at Hour 0 and at approximately 12 hours later on Days 1 through 9 with one dose at Hour 0 on Day 10. Dosing on Days 2 through 10 occurred within ±1 hour of dosing times on Day 1. The doses in part B are as follows:

Cohort B1: 100 mg the compound of formula (I) (1×100-mg capsule) or matching placebo BID, for a total daily dose of 200 mg (except for Day 10 which has a total daily dose of 100 mg)

Cohort B2: 300 mg the compound of formula (I) (3×100 mg capsules) or matching placebo BID, for a total daily dose of 600 mg (except for Day 10 which has a total daily dose of 300 mg)

Cohort B3: 1000 mg the compound of formula (I) (10×100 mg capsules) or matching placebo BID, for a total daily dose of 2000 mg (except for Day 10 which has a total daily dose of 1000 mg).

Study Agent

The study drug product was supplied as 10- and 100-mg powder-in-capsule (PIC) consisting of the compound of formula (I) as drug substance in size 00 Swedish Orange, opaque, hydroxypropyl methylcellulose (HPMC) capsule. The capsules were packaged open-labelled in high density polyethylene (HDPE) bottles. Study drug product was prepared and labeled in blinded fashion by the unblinded pharmacy staff (or designee) at the time of dispensing.

Study Assessments

Safety Assessments

Safety was determined by evaluating physical examinations, vital signs, safety 12-lead electrocardiograms (ECGs) monitoring, clinical laboratory tests, and adverse events (AEs). For procedures scheduled to be performed at common times, collection of PK samples was collected as close as possible to the designated time. The cardiodynamic recordings via ECG extractions from the Holter monitor were conducted as close as possible prior to the corresponding PK sampling. Vital signs, followed by safety ECGs, were be taken before the PK sampling (or before the cardiodynamic sampling if scheduled at the same time), unless PK samples were late as a result in which case vital signs were taken following the PK sampling.

Pharmacokinetic Assessments

For all subjects, blood samples for the determination of plasma concentration of the compound of formula (I) were collected at scheduled time points. Blood samples were analyzed to calculate different plasma PK parameters in both part A and part B.

Urine samples for the determination of concentration of the compound of formula (I) were collected at various posedose intervals only in part A.

Immunophenotyping was conducted on NK Cells in part B only.

Statistical Methods

Safety analyses were performed using the Safety analysis set. Safety variables include vital signs, adverse events, clinical laboratory results (hematology, chemistry, coagulation, and urinalysis), and ECG parameters, such as Friderica's corrected QT interval (QTcF), PR interval, QT interval, QRS interval, and heart rate, from standard safety digital ECGs. Vital signs were summarized in terms of observed values and changes from baseline.

For all PK data analyses, the PK analysis set was used. Individual subject and mean plasma drug concentration versus time curves for the compound of formula (I) were presented for each dose group. Summary statistics (mean, standard deviation, coefficient of variation, median, minimum, maximum, geometric mean, geometric coefficient of variation, number of subjects) were calculated for plasma concentrations at each time point for each dose group, and the PK parameters for each dose group. Urine PK parameters were summarized for exploratory purposes.

Subjects

Thirty-two subjects (16 male, 16 female) with mean (range) age of 35 (19-55) years and body weight of 74 (53-111) kg participated in the part A (SAD) study, and 24 subjects (20 male, 4 female) with mean (range) age of 34 (20-52) years and body weight 83 (66-109) kg participated in the part B (MAD) study.

Safety Results

The treatment emergent adverse events (TEAE5) in part A and part B are summarized in Tables 1 and 2.

TABLE 1

TEAEs in the SAD cohorts in Part A

| SAD | 100 mg (n = 6) | 300 mg (n = 6) | 1000 mg (n = 6) | 2000 mg (n = 6) | Placebo (n = 8) | Overall (N = 32) |
|---|---|---|---|---|---|---|
| Subjects with TEAEs | | | | | | |
| Any TEAE | 4 (67) | 2 (33) | 2 (33) | 3 (50) | 2 (25) | 13 (41) |
| Moderate or severe TEAE | 0 | 0 | 0 | 0 | 0 | 0 |
| Seriou TEAE | 0 | 0 | 0 | 0 | 0 | 0 |
| TEAE leading to discontinuation | 0 | 0 | 0 | 0 | 0 | 0 |
| Most frequent TEAEs[a] | | | | | | |
| Pain in extremity | 3 (50) | 1 (17) | 0 | 0 | 0 | 4 (13) |
| Back pain | 1 (17) | 0 | 1 (17) | 0 | 1 (13) | 3 (9) |
| Apthous ulcer | 1 (17) | 0 | 0 | 1 (17) | 0 | 2 (6) |
| Diarrhea | 0 | 0 | 1 (17) | 1 (17) | 0 | 2 (6) |
| Headache | 1 (17) | 0 | 0 | 1 (17) | 0 | 2 (6) |
| Total number of TEAEs | 8 | 2 | 6 | 6 | 3 | 25 |

[a]Events occurring in ≥2 subjects (>5%) in the entire population.

TABLE 2

TEAEs in the MAD cohorts in Part B

| MAD | 100 mg (n = 6) | 300 mg (n = 6) | 1000 mg (n = 6) | Placebo (n = 6) | Overall (N = 24) |
|---|---|---|---|---|---|
| Subjects with TEAEs | | | | | |
| Any TEAE | 5 (83) | 1 (17) | 0 | 4 (67) | 10 (42) |
| Moderate or severe TEAE | 0 | 0 | 0 | 0 | 0 |
| Serious TEAE | 0 | 0 | 0 | 0 | 0 |
| TEAE leading to discontinuation | 0 | 0 | 0 | 0 | 0 |
| Most frequent TEAEs[a] | | | | | |
| Pain in extremity | 1 (17) | 0 | 0 | 1 (17) | 2 (8) |
| Dizziness | 2 (33) | 0 | 0 | 0 | 2 (8) |
| Headache | 2 (33) | 0 | 0 | 0 | 2 (8) |
| Acne | 1 (17) | 0 | 0 | 1 (17) | 2 (8) |
| Total number of TEAEs | 11 | 9 | 0 | 5 | 25 |

[a]Events occurring in ≥2 subjects (>5%) in the entire population.

No serious AEs were reported in either the SAD or MAD cohorts. All reported treatment-emergent AEs were mild in severity. Three AEs (out of 25 reported in 13 of 32 subjects) in the SAD cohorts and 1 AE (out of 25 reported in 10 of 24 subjects) in the MAD cohorts were considered related to study drug: diarrhea, abdominal discomfort, and vomiting (2000 mg, SAD), and abdominal pain (placebo, MAD). No clinically significant changes from predose baseline in laboratory assessments (in particular lipid, coagulation, and hematology), vital signs or ECGs were observed at any time point postdose in either the SAD or MAD cohorts.

NK Cells Counts:

As demonstrated in FIGS. 10A-B, there were no apparent changes in absolute or relative NK cell counts from day 1 to day 10 in the part B (MAD) study, suggestive of a lack of a systemic immunosuppressive effect of the compound of formula (I).

Pharmacokinetics Results

Figure 11A:
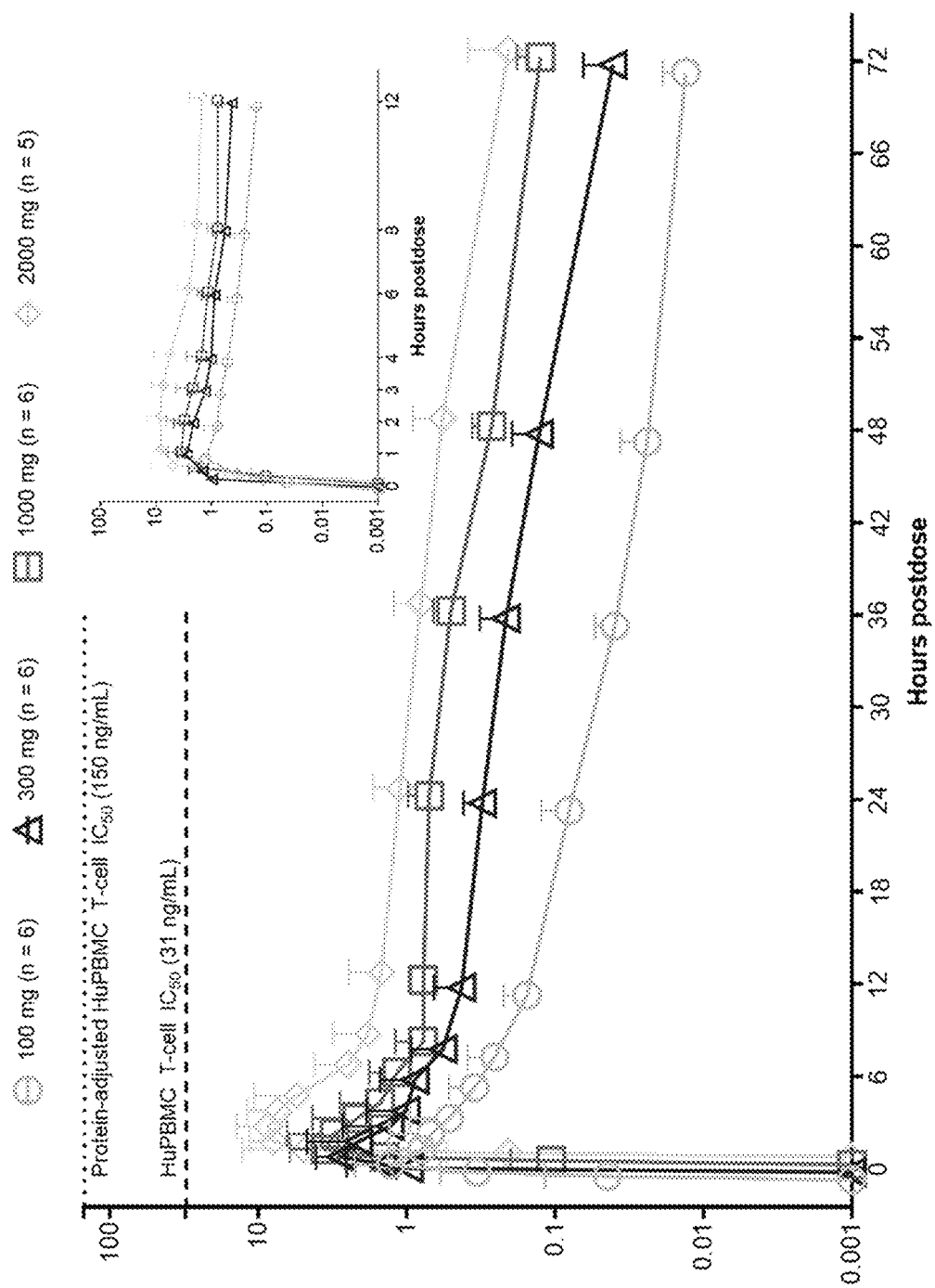
FIGS. 11A-B demonstrate the plasma concentrations of the compound of formula (I) including mean and standard deviation (SD), following dosing in the single ascending dose (SAD) cohorts (FIG. 11A) and MAD cohorts (FIG. 11B).
Figure 11B:
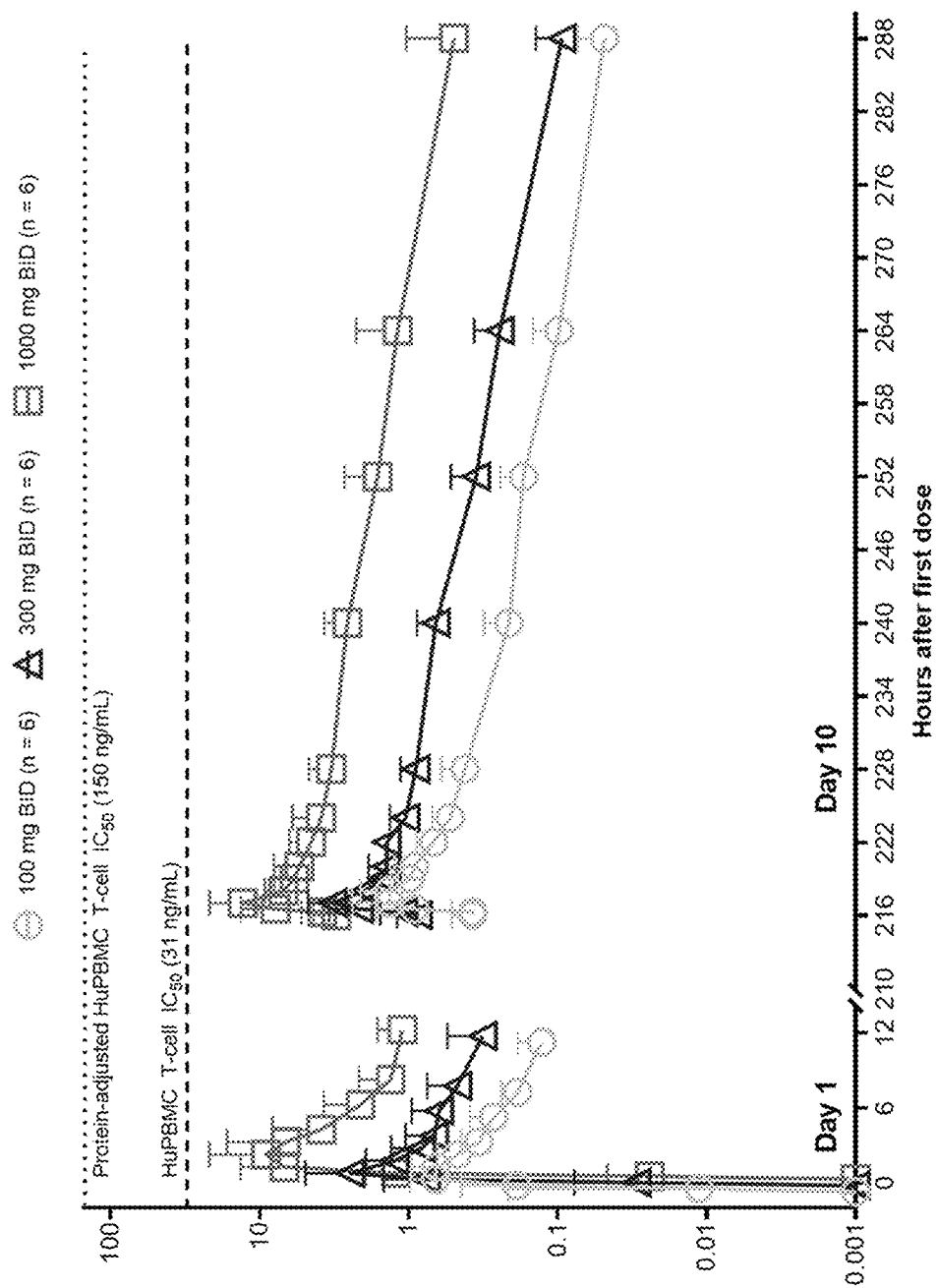

Plasma Pharmacokinetic Parameters:

Pharmacokinetic parameters of the compound of formula (I) during the studies were listed in Tables 3 and 4, and the plasma concentrations were demonstrated in FIGS. 11A-B.

TABLE 3

Pharmacokinetic parameters of Compound of formula (I) following a single dose

| | 100 mg (n = 6) | 300 mg (n = 6) | 1000 mg (n = 6)[a] | 2000 mg (n = 6) |
|---|---|---|---|---|
| Plasma Parameters | | | | |
| $T_{max}$, hours, median (min, max) | 1.0 (1.0, 2.0) | 1.0 (1.0, 2.0) | 1.0 (0.5, 2.0) | 2.0 (0.5, 4.0) |
| $C_{max}$, ng/mL, mean (SD) | 1.3 (0.94) | 3.4 (2.3) | 4.8 (3.3) | 10.1 (5.9) |
| $t_{1/2}$, hours, mean (SD) | 17.5 (5.2) | 14.5 (2.1) | 16.6 (4.4) | 16.6 (4.5) |
| $AUC_{inf}$, ng*hr/mL[b], mean (SD) | 8.4 (4.4) | 24.6 (13.6) | 47.0 (16.4) | 96.0 (52.5) |
| Urine parameter | | | | |
| $fe_{0-72}$, %, mean (SD) | 0.10 (0.051) | 0.082 (0.025) | 0.056 (0.025) | 0.063 (0.028) |

[a]One subject was excluded from descriptive statistics of $AUC_{inf}$ and $t_{1/2}$ because the terminal elimination phase could not be robustly characterized.
[b]Less than on 6% on average of the total $AUC_{inf}$ was extrapolated.
$AUC_{inf}$, area under the concentration-time curve from zero to infinity;
$C_{max}$, maximum plasma concentration;
$fe_{0-72}$, percentage of dose excreted in urine over the cumulative interval of 0 to 72 hours;
max, maximum;
min, minimum;
SD, standard deviation;
$t_{1/2}$, half-life;
$T_{max}$, time to $C_{max}$.

TABLE 4

Plasma pharmacokinetic parameters of the compound of formula (I) following multiple dosing

|  | 100 mg BID (n = 6) | 300 mg BID (n = 6) | 1000 mg BID (n = 6) |
|---|---|---|---|
| Day 1 (morning dose) | | | |
| $T_{max}$, hours, median (min, max) | 1.5 (0.50, 3.0) | 1.0 (0.50, 2.0) | 1.5 (1.0, 2.0) |
| $C_{max}$, ng/mL, mean (SD) | 0.78 (0.33) | 2.6 (2.4) | 10.7 (12.8) |
| $AUC_{0-12}$, ng*hr/mL, mean (SD) | 3.5 (1.2) | 8.5 (4.8) | 37.4 (38.7) |
| Day 10 (morning dose) | | | |
| $T_{max,ss}$, hours, median (min, max) | 2.0 (0.58, 4.0) | 1.0 (0.50, 1.0) | 1.0 (0.25, 1.0) |
| $C_{max,ss}$, ng/mL, mean (SD) | 1.7 (0.80) | 3.5 (1.4) | 13.3 (8,4) |
| $AUC_{0-12,ss}$, ng*hr/mL, mean (SD) | 8.9 (3.6) | 16.9 (3.7) | 62.1 (23.4) |
| $t_{1/2}$, hours, mean (SD) | 19.8 (3.7) | 19.2 (2.6) | 18.5 (6.1) |
| Dose normalized parameters Day 1 | | | |
| $C_{max}/D$, ng/mL/mg, mean (SD) | 0.0078 (0.0033) | 0.0086 (0.0079) | 0.011 (0.013) |
| $AUC_{0-12}/D$, ng*hr/mL/mg, mean (SD) | 0.035 (0.012) | 0.028 (0.016) | 0.037 (0.039) |
| Day 10 | | | |
| $C_{max,ss}/D$, ng/mL/mg, mean (SD) | 0.017 (0.0080) | 0.012 (0.0045) | 0.013 (0.0084) |
| $AUC_{0-12,ss}/D$, ng*hr/mL/mg, mean (SD) | 0.089 (0.036) | 0.056 (0.012) | 0.062 0.023) |
| Accumulation ratio[a] | | | |
| Mean (SD) | 2.6 (0.78) | 2.5 (1.1) | 2.9 (1.7) |
| Geometric mean (CV %) | 2.5 (35.2) | 2.3 (51.9) | 2.3 (92.5) |

[a] Calculated as $AUC_{0-12,ss}/AUC_{0-12}$.
AUC, area under the concentration-time curve;
$AUC_{0-12}$, AUC from time 0 to 12 hours after first dose on day 1;
$AUC_{0-12,ss}$, AUC from 0 to 12 hours postdose at steady state;
BID, twice daily;
$C_{max}$, maximum plasma concentration;
$C_{max,ss}$, $C_{max}$ at steady state;
CV %, coefficient of variation;
D, dose;
max, maximum;
min, minimum;
SD, standard deviation;
$t_{1/2}$, half-life;
$T_{max}$, time to $C_{max}$.

Plasma concentrations of the compound of formula (I) were low (<35 ng/ml) following single oral doses up to 2000 mg and multiple doses up to 1000 mg BID (FIGS. 11A-B). In particular, the average $C_{max}$ at single dose of 2000 mg was 10 ng/ml, and the highest observed $C_{max}$ across all doses was 34.34 ng/ml.

Urinary excretion of the compound of formula (I) was low, averaging <0.1% at all single-dose levels (Table 3).

Exposure (AUC and $C_{max}$) increased in a slightly less than dose proportional fashion across the studied single-dose range, and dose proportionally after multiple-dose administration. Drug accumulation after BID dosing for 10 days was similar across all MAD dose cohorts, averaging between 2.5- and 2.9-fold. This degree of accumulation was consistent with the observed mean terminal elimination half-life, which was independent of dose and ranged from 15 to 20 hours across all doses in the SAD and MAD cohorts (Tables 3 and 4).

Steady state was attained after 7 days of dosing following 100 mg BID and after 3 days of dosing following 300 mg and 1000 mg BID.

In the part A (SAD) study, the area under the concentration time curve from time 0 extrapolated to infinity ($AUC_{0-inf}$) in the plasma of the subjects ranges from about 2.70 ng.hr/mL to about 172 ng.hr/mL, and the average $AUC_{0-inf}$ is from about 8.38 ng.hr/mL to about 96.0 ng.hr/mL.

In the part B (MAD) study, the area under the concentration time curve from time 0 to the 12 hour time point at steady-state ($AUC_{ss0-12}$) in the plasma of the subjects ranges from about 5.43 ng.hr/mL to about 88.5 ng.hr/mL, and the average $AUC_{ss0-12}$ is from about 8.94 ng.hr/mL to about 62.1 ng.hr/mL.

Conclusions

The compound of formula (I) was generally well-tolerated as a single dose up to 2000 mg and as multiple doses up to 1000 mg BID for 10 days. Consistent with a gut-selective approach, steady-state systemic exposures at the highest tested dose (1000 mg BID) were low with mean $C_{max,ss}$ (maximum observed concentration at steady-state, 13 ng/ml) approximately 11-fold below the protein-adjusted JAK3 $IC_{50}$ (150 ng/ml).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present inventions as defined by the specific description.

The invention claimed is:

1. A method of safely administering a compound of formula (I)

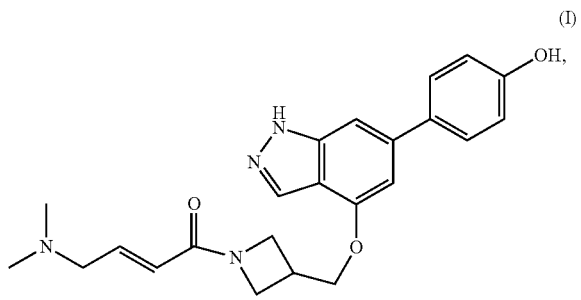 [SMILES: CN(C)C/C=C/C(=O)N1CC(COc2cc(-c3ccc(O)cc3)cc3[nH]ncc23)C1]

or a pharmaceutically acceptable salt thereof, to a human subject in need thereof, comprising orally administering to the subject a pharmaceutical composition comprising the compound of formula (I) or the pharmaceutically acceptable salt thereof and a pharmaceutically acceptable carrier, wherein a total dosage of the compound of formula (I) or the pharmaceutically acceptable salt thereof administered is about 100 mg to about 2000 mg per administration.

2. The method of claim 1, wherein the total dosage of the compound of formula (I) or the pharmaceutically acceptable salt thereof administered per administration is about 100 mg, 150 mg, 200 mg, 300 mg, 400 mg, 500 mg, 600 mg, 700 mg, 800 mg, 900 mg, 1000 mg, 1250 mg, 1500 mg, 1750 mg, or 2000 mg, or any dosage in between.

3. The method of claim 1, wherein the pharmaceutical composition is orally administered once per day.

4. The method of claim 1, wherein the pharmaceutical composition is orally administered once per day, and the total dosage of the compound of formula (I) or the pharmaceutically acceptable salt thereof administered per day is about 100 mg, 150 mg, 200 mg, 300 mg, 400 mg, 500 mg, 600 mg, 700 mg, 800 mg, 900 mg, 1000 mg, 1250 mg, 1500 mg, 1750 mg, or 2000 mg, or any dosage in between.

5. The method of claim 1, wherein the pharmaceutical composition is orally administered twice per day.

6. The method of claim 1, wherein the pharmaceutical composition is orally administered twice per day, and the total dosage of the compound of formula (I) or the pharmaceutically acceptable salt thereof administered per administration is about 100 mg, 150 mg, 200 mg, 300 mg, 400 mg, 500 mg, 600 mg, 700 mg, 800 mg, 900 mg, or 1000 mg, or any dosage in between.

7. The method of claim 1, wherein the pharmaceutical composition is orally administered twice per day, and the total dosage of the compound of formula (I) or the pharmaceutically acceptable salt thereof administered per day is about 200 mg, 300 mg, 400 mg, 500 mg, 600 mg, 700 mg, 800 mg, 900 mg, 1000 mg, 1250 mg, 1500 mg, 1750 mg, or 2000 mg, or any dosage in between.

8. The method of claim 1, wherein the administration of the pharmaceutical composition does not result in a serious adverse effect.

9. The method of claim 8, wherein the serious adverse effect is selected from the group consisting of a thromboembolic event, a malignancy, lymphopenia, neutropenia, liver enzyme elevation, lipid elevation, serum creatinine elevation, and a serious infection.

10. The method of claim 1, wherein the administration of the pharmaceutical composition does not result in clinically significant changes from the predose baseline in a laboratory assessment, a vital sign or an electrocardiogram (ECG).

11. The method of claim 1, wherein the pharmaceutical composition is orally administered once per day, and the administration of the pharmaceutical composition achieves, in the plasma of the subject, an area under the concentration time curve from time 0 extrapolated to infinity ($AUC_{0-inf}$) of about 2.70 ng.hr/mL to about 172 ng.hr/mL.

12. The method of claim 1, wherein the pharmaceutical composition is orally administered twice per day, and the administration of the pharmaceutical composition achieves, in the plasma of the subject, an area under the concentration time curve from time 0 to 12 hour time point at steady-state ($AUC_{ss0-12}$) of about 5.43 ng.hr/mL to about 88.5 ng.hr/mL.

13. The method of claim 1, wherein the administration of the pharmaceutical composition achieves, in the plasma of the subject, a maximum concentration observed ($C_{max}$) of not more than about 25 ng/mL.

14. The method of claim 1, wherein the pharmaceutical composition is orally administered twice per day, and achieves a steady-state condition of the compound of formula (I) within 7 days after the second administration when the total dosage per administration is about 100 mg, or achieves a steady-state condition of the compound of formula (I) within 3 days after the second administration when the total dosage per administration is about 300 mg to about 1000 mg.

15. The method of claim 14, wherein the pharmaceutical composition achieves a maximum observed concentration at steady-state ($C_{max,ss}$) of not more than about 25 ng/mL.

16. The method of claim 1, wherein the administration of the pharmaceutical composition achieves a mean terminal elimination half-life of about 11 to 30 hours.

17. The method of claim 1, wherein the pharmaceutical composition is orally administered once per day and achieves a urinary excretion of the compound formula (I) of not more than 1%.

18. The method of claim 1, wherein the human subject is in need of a treatment of a gastrointestinal inflammatory disease.

19. A method of treating a gastrointestinal inflammatory disease in a human subject in need thereof, the method comprising orally administering to the subject a compound of formula (I):

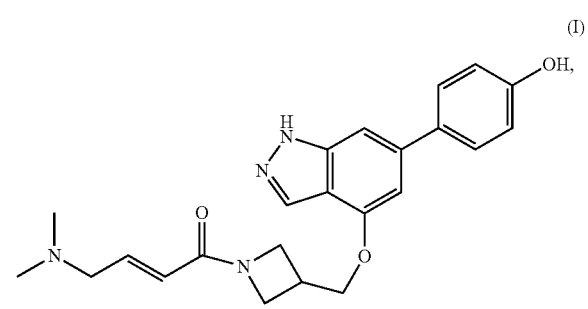 [SMILES: CN(C)C/C=C/C(=O)N1CC(COc2cc(-c3ccc(O)cc3)cc3[nH]ncc23)C1]

or a pharmaceutically acceptable salt thereof, wherein the compound of formula (I) or the pharmaceutically acceptable salt is administered to the subject in an amount sufficient to provide from about 500 mg per day to about 2000 mg per day of the compound of formula (I) or a pharmaceutically acceptable salt thereof.

20. A method of treating celiac disease in a human subject in need thereof, the method comprising orally administering to the subject a compound of formula (I):

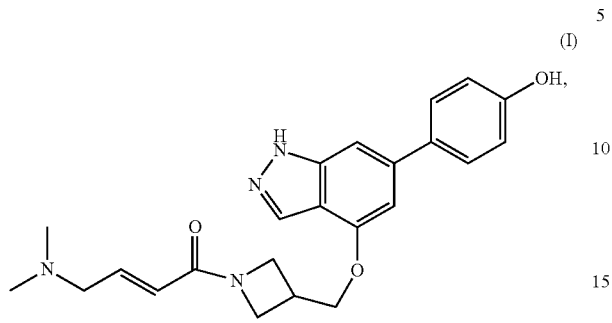

or a pharmaceutically acceptable salt thereof, wherein the compound of formula (I) or the pharmaceutically acceptable salt is administered to the subject in an amount sufficient to provide from about 500 mg per day to about 2000 mg per day of the compound of formula (I) or a pharmaceutically acceptable salt thereof.

* * * * *